(12) United States Patent
Stokbroekx et al.

(10) Patent No.: US 8,143,402 B2
(45) Date of Patent: Mar. 27, 2012

(54) POLYMORPHIC FORMS OF A MACROCYCLIC INHIBITOR OF HCV

(75) Inventors: Sigrid Carl Maria Stokbroekx, Beerse (BE); Carina Leys, Stabroek (BE); Kelly Ann Swinney, Pulle (BE); Stijn Wuyts, Oostham (BE); Andras Horvath, Turnhout (BE)

(73) Assignee: Tibotec Pharmaceuticals Ltd., Little Island, Co Cork (IE)

( * ) Notice: Subject to any disclaimer, the term of this patent is extended or adjusted under 35 U.S.C. 154(b) by 346 days.

(21) Appl. No.: 12/518,548

(22) PCT Filed: Feb. 1, 2008

(86) PCT No.: PCT/EP2008/051268
§ 371 (c)(1),
(2), (4) Date: Jun. 10, 2009

(87) PCT Pub. No.: WO2008/092954
PCT Pub. Date: Aug. 7, 2008

(65) Prior Publication Data
US 2010/0029715 A1      Feb. 4, 2010

(30) Foreign Application Priority Data
Feb. 1, 2007   (EP) .................................. 07101563

(51) Int. Cl.
*C07D 215/38*   (2006.01)
(52) U.S. Cl. .................. 546/153; 546/167; 514/312
(58) Field of Classification Search .................. 546/153, 546/167; 514/312
See application file for complete search history.

(56) References Cited

U.S. PATENT DOCUMENTS
7,671,032 B2 *   3/2010   Rosenquist et al. ........... 514/1.1

FOREIGN PATENT DOCUMENTS
WO   WO 2005/073195   8/2005
WO   WO 2007/014926   2/2007

OTHER PUBLICATIONS

Bernstein, J. et al. "Concomitant Polymorphs". Angewandte Chemie. International Edition, Wiley VCH Verlag, Weinheim, DE., vol. 38, 1999, pp. 3441-3461, XP002219563.
Caira, M.R. "Crystalline Polymorphism of Organic Compounds". Topics in Current Chemistry, Springer, Berlin, DE., vol. 198, 1998, pp. 163-208, XP001156954.

* cited by examiner

*Primary Examiner* — D M Seaman
(74) *Attorney, Agent, or Firm* — Andrea Jo Kamage

(57) ABSTRACT

Provided are crystalline forms of the compound of formula (I), which is a macrocyclic inhibitor of HCV, processes for the preparation thereof, and pharmaceutical compositions comprising these crystalline forms.

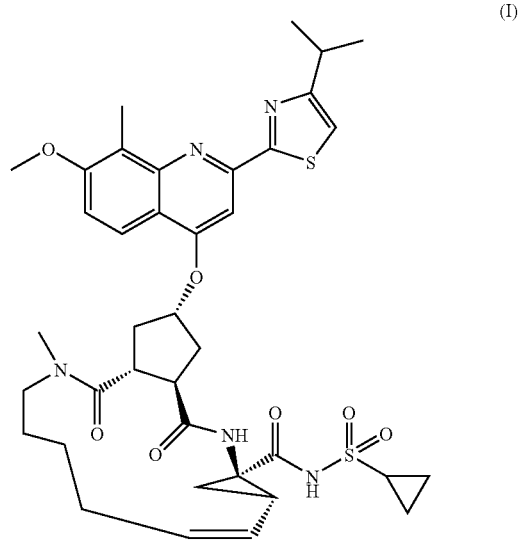

(I)

26 Claims, 15 Drawing Sheets

POLYMORPHIC FORMS OF A MACROCYCLIC INHIBITOR OF HCV

CROSS REFERENCE TO RELATED APPLICATIONS

This application is the national stage of PCT Application No. PCT/EP2008/051268 filed Feb. 1, 2008, which claims priority from European Patent Application No. 07101563.0, filed Feb. 1, 2007, the entire disclosures of which are hereby incorporated in their entirety.

FIELD OF THE INVENTION

The present invention relates to crystalline forms of a macrocyclic inhibitor of HCV.

BACKGROUND OF THE INVENTION

Hepatitis C virus (HCV) is the leading cause of chronic liver disease worldwide. Following initial acute infection, a majority of infected individuals develop chronic hepatitis because HCV replicates preferentially in hepatocytes but is not directly cytopathic. Chronic hepatitis can progress to liver fibrosis leading to cirrhosis, end-stage liver disease, and HCC (hepatocellular carcinoma), making it the leading cause of liver transplantations. This and the number of patients involved, has made HCV the focus of considerable medical research. Replication of the genome of HCV is mediated by a number of enzymes, amongst which is HCV NS3 serine protease and its associated cofactor, NS4A. NS3 serine protease is considered to be essential for viral replication and has become an attractive target for drug discovery.

Current anti-HCV therapy is based on (pegylated) interferon-alpha (IFN-α) in combination with ribavirin. Not only does this therapy result in a limited efficacy in that only part of the patients are treated successfully, but it also faces significant side effects and is poorly tolerated in many patients. Hence there is a need for further HCV inhibitors that overcome the disadvantages of current HCV therapy such as side effects, limited efficacy, the emergence of resistance, as well as compliance failures.

Various agents have been described that inhibit HCV NS3 serine protease. WO 05/073195 discloses linear and macrocyclic NS3 serine protease inhibitors with a central substituted proline moiety and WO 05/073216 with a central cyclopentyl moiety. Amongst these, the macrocyclic derivatives are attractive by overcoming one or more of the disadvantages of current anti-HCV therapy.

It has been found that the compound of formula (I), with the structure depicted hereafter, is particularly suited for use in anti-HCV therapy:

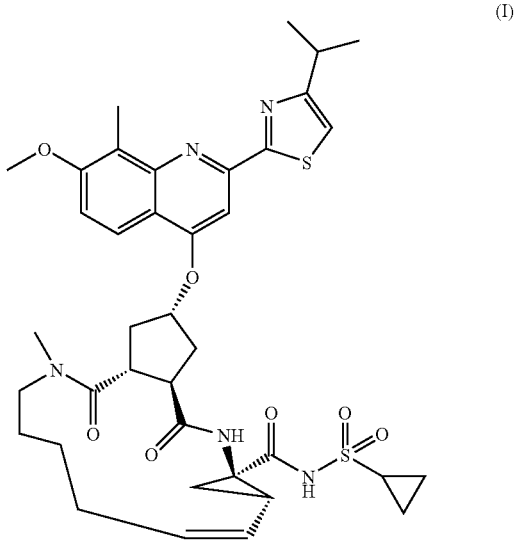

The compound of formula (I) is an inhibitor of the Hepatitis C virus (HCV) serine protease and is described in WO 2007/014926, published on 8 Feb. 2007. This compound overcomes several of the disadvantages of current anti-HCV therapy and in particular shows pronounced activity against HCV, has an attractive pharmacokinetic profile, and is well-tolerated. Following the synthesis procedure described in Example 5 of WO 2007/014926, an amorphous solid form is obtained.

It now has been found that the compound of formula (I) can be converted into crystalline forms, which can advantageously be used as active ingredients in anti-HCV therapy. To that purpose, these crystalline forms are converted into pharmaceutical formulations.

An amorphous form is a form in which a three-dimensional long-range order does not exist. In the amorphous form the position of the molecules relative to one another are essentially random, i.e. without regular arrangement of the molecules in a lattice structure. Amorphous materials may have interesting properties, but generating and stabilising this state usually offers difficulties in that the crystalline state typically is the more stable state. Compounds in amorphous form can convert partially or completely to crystalline forms over time or under the influence of external factors such as temperature, humidity, traces of crystalline material in the environment, etc. Usually a crystalline form of an active ingredient is preferred in the manufacture and storage of pharmaceutical dosage forms.

A crystal or crystalline form is the form in which the position of the molecules relative to one another is organised according to a three-dimensional lattice structure. Crystalline forms may include polymorphs and pseudopolymorphs. Polymorphs are different crystalline forms of the same compound resulting from a different arrangement of the molecules in the solid state. Polymorphs differ from each other in their physicochemical properties but not in their chemical composition. Polymorphism can be difficult to control and may pose challenges to the development of pharmaceutical dosage forms. The term pseudopolymorphs refers to different crystal forms due to different amounts or types of solvent in the lattice structure of a compound.

Solid state chemistry is of interest to the pharmaceutical industry, in particular as concerns the development of suitable dosage forms. Solid state transformations may seriously impact the stability of pharmaceuticals (shelf-life). A metastable pharmaceutical solid form can change into a crystalline structure (e.g. from amorphous to crystalline) or solvate/desolvate in response to changes in environmental conditions, processing, or over time.

Different crystal forms or the amorphous form of a given drug may have substantial differences in such pharmaceutically important properties as dissolution rate, thermodynamic solubility, and bioavailability. The rate of dissolution of an active ingredient in a patient's stomach fluid may have therapeutic consequences since it imposes an upper limit on the rate at which an orally-administered active ingredient may reach the patient's bloodstream. The rate of dissolution is thus a consideration in formulating solid and liquid dosage forms. Likewise, different solid forms may have different processing properties, such as hygroscopicity, flowability, compactation, and the like, which could affect their suitability as active pharmaceuticals for commercial production.

During the clinical development of pharmaceutical drugs, if the polymorphic form is not held constant, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations.

It is an object of the present invention to provide the HCV inhibitory agent of formula (I) in a crystalline form having beneficial properties in terms of one or more of the following: the ability to be formulated, to be stored and to be administered as to effectively excert its antiviral properties.

DESCRIPTION OF THE INVENTION

Figure 1:
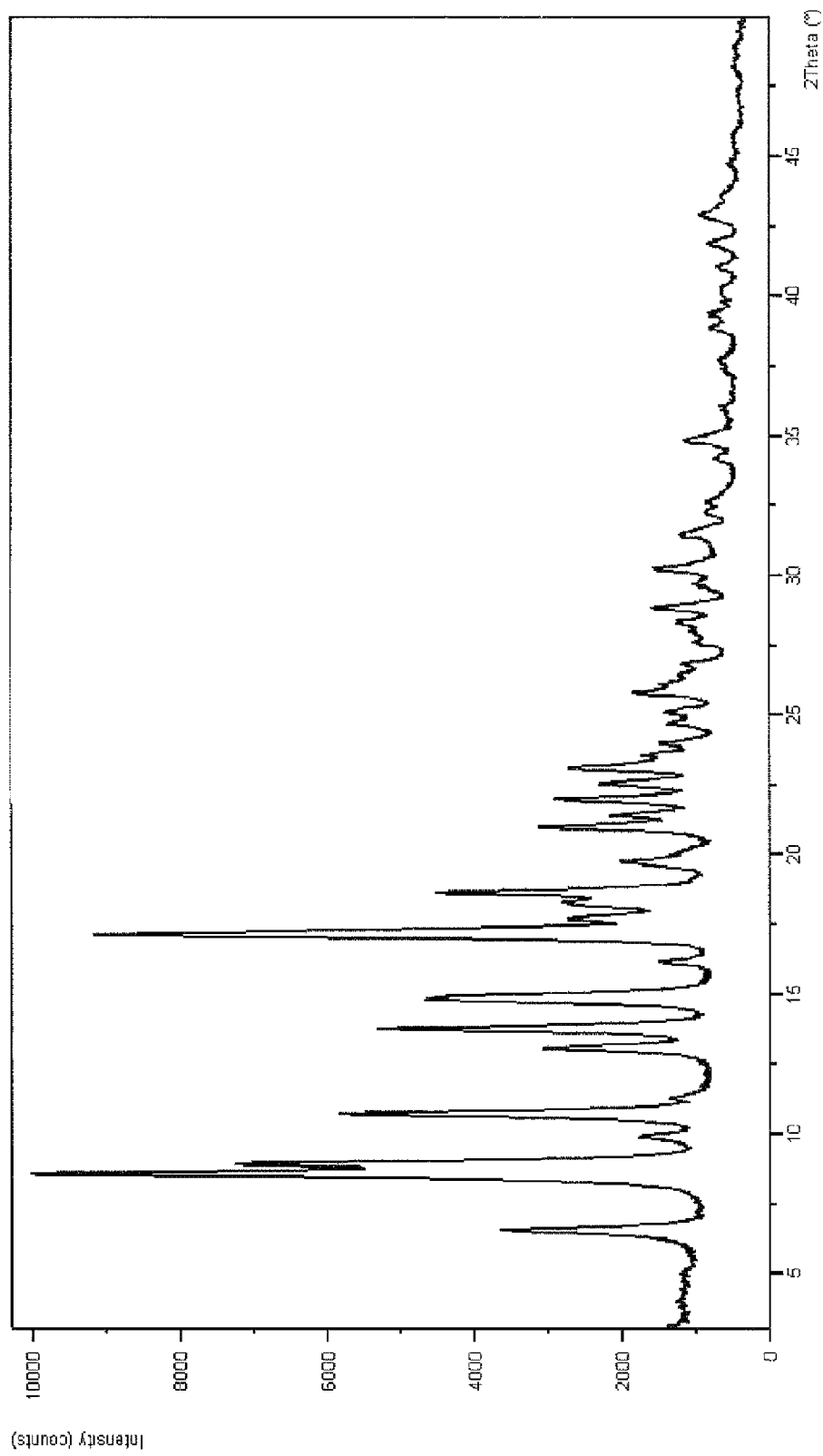
FIG. 1 is an X-ray powder Diffraction (XPRD) pattern representation of Form I

The present invention relates to an HCV inhibitor, which is the compound of formula (I) in crystalline form. The invention in particular concerns the crystalline forms denominated Form I, Form II, Form III, Form IV, Form V, and Form VI. These forms are as characterized hereinafter. Of special interest are Form I and Form II.

In one embodiment, the invention concerns the crystalline form of the compound of formula (I), that is denominated as Form I of the compound of formula (I), or in short "Form I". This form has the X-ray powder diffraction and the IR pattern mentioned herebelow.

Form I has an X-ray powder diffraction pattern comprising peaks at 8.5°±0.2°, 10.7°±0.2°, and 17.1±0.2° two theta. Form I is characterized by typical diffraction peaks at two-theta positions 8.5°±0.2°, 10.7°±0.2°, 13.7°±0.2°, 14.8°±0.2° and 17.1°±0.2°. Form I is further characterized by X-ray powder diffraction peaks at two-theta positions 6.51°±0.2°, 8.90±0.2°, 13.0°±0.2°, 18.60±0.2° and 21.0°±0.2°. Form I has an IR pattern comprising peaks at 3405±1 cm$^{-1}$, 3066±1 cm$^{-1}$, 1517±1 cm$^{-1}$, 1427±1 cm$^{-1}$, 1301±1 cm$^{-1}$, 1285±1 cm$^{-1}$, 1149±1 cm$^{-1}$, 1132±1 cm$^{-1}$, 1111±1 cm$^{-1}$, 975±1 cm$^{-1}$, 956±1 cm$^{-1}$, and 800±1 cm$^{-1}$. Or, Form I has an IR pattern comprising peaks at: 3405(w), 3066(w), 1712(m), 1665(m), 1517(s), 1427(s), 1387(m), 1351(vs), 1300(m), 1285(m), 1132(s), 1111(vs), 1082(m), 1072(m), 1049(s), 975 (m), 885(s), 872(s), 838(s), 813(s), 800(s), 760(m) and 742 (m), wherein these numbers are expressed in wave numbers (cm$^{-1}$) and m is medium intensity, s is strong intensity and vs is very strong intensity.

In another embodiment, the invention concerns the crystalline form of the compound of formula (I), that is denominated as Form II of the compound of formula (I), or in short "Form II". This form has the X-ray powder diffraction and the IR pattern mentioned herebelow.

Form II has an X-ray powder diffraction pattern comprising peaks at 6.5°±0.2°, 10.2°±0.2°, 12.9°±0.2°, and 14.4°±0.2 two theta. Form II is characterized by typical diffraction peaks at two-theta positions 4.6°±0.2°, 6.50±0.2°, 10.2°±0.2°, 12.9°±0.2° and 14.4°+0.2. Form II is further characterized by X-ray powder diffraction peaks at two-theta positions 9.1°±0.2°, 16.5°±0.2°, 18.1°+0.2°, 20.4°±0.2° and 22.8°+0.2°. Form II has an IR pattern comprising peaks at 1592 cm$^{-1}$±1 cm$^{-1}$. Or, Form II has an IR pattern comprising peaks at: 1711(m), 1435(s), 1349(s), 1065(m), 1038(m), 881(s), 873(s), 834(m) and 746(m), wherein these numbers are expressed in wave numbers (cm$^{-1}$) and m, s and vs are as specified above.

In another embodiment, the invention concerns the crystalline form of the compound of formula (I), that is denominated as Form III of the compound of formula (I), or in short "Form III". This form has the X-ray powder diffraction and the IR pattern mentioned herebelow.

Form III has an X-ray powder diffraction pattern comprising peaks at 9.8°±0.2° and 17.8°±0.2° two theta. Form III is characterized by typical diffraction peaks at two-theta positions 6.5°±0.2°, 9.80±0.2° and 17.8°±0.2°. Form III is further characterized by X-ray powder diffraction peaks at two-theta positions 8.6°±0.2°, 10.60±0.2°, 11.7°±0.2°, 12.9°±0.2°, 13.7°±0.2°, 14.8°±0.2° and 19.5°+0.2°. Form III has an IR pattern comprising peaks at 3120±1 cm$^{-1}$, 2870±1 cm$^{-1}$, and 1063 cm$^{-1}$±1 cm$^{-1}$. Or, Form III has an IR pattern comprising peaks at: 1718(m), 1664(m), 1434(s), 1353(s), 1113(s), 1076 (m), 1063(m), 1039(s), 881(s), 836(s), 810(m), 799(m) and 758(m), wherein these numbers are expressed in wave numbers (cm$^{-1}$) and m, s and vs are as specified above.

In another embodiment, the invention concerns the crystalline form of the compound of formula (I), that is denominated as Form IV of the compound of formula (I), or in short "Form IV". This form has the X-ray powder diffraction and the IR pattern mentioned herebelow.

Form IV has an X-ray powder diffraction pattern comprising peaks at 9.6°±0.2°, 11.8°±0.2°, and 17.1°±0.2° two theta. Form IV is characterized by typical diffraction peaks at two-theta positions 5.6°±0.2°, 9.6°±0.2°, 11.8°±0.2°, 15.9°±0.2° and 17.1°±0.2°. Form IV is further characterized by X-ray powder diffraction peaks at two-theta positions 6.8°±0.2°, 7.8°±0.2°, 11.1°±0.2°, 13.0°±0.2° and 14.4°±0.2°. Form IV has an IR pattern comprising peaks at 1369±1 cm$^{-1}$ and 846±1 cm$^{-1}$. Or, Form IV has an IR pattern comprising peaks at: 1713(m), 1436(s), 1348(s), 1075(m), 1038(s), 883(s), 872(s), 801(m) and 743(m), wherein these numbers are expressed in wave numbers (cm$^{-1}$) and m, s and vs are as specified above.

In another embodiment, the invention concerns the crystalline form of the compound of formula (I), that is denominated as Form V of the compound of formula (I), or in short "Form V". This form has the X-ray powder diffraction and the IR pattern mentioned herebelow.

Form V has an X-ray powder diffraction pattern comprising peaks at 9.6°±0.2° and 19.0°±0.2° two theta.

In another embodiment, the invention concerns the crystalline form of the compound of formula (I), that is denominated as Form V of the compound of formula (I), or in short "Form V". This form has the X-ray powder diffraction and the IR pattern mentioned herebelow.

Form VI has an X-ray powder diffraction pattern comprising peaks at 4.4°±0.2°, 16.5°±0.2°, 9.90±0.2°, 10.5°+±0.2°, and 12.9°±0.2° two theta. Form VI is characterized by typical diffraction peaks at two-theta positions 4.4°±0.2°, 6.5°±0.2°, 9.9°±0.2°, 10.5°±0.2° and 12.9°±0.2°. Form VI is further characterized by X-ray powder diffraction peaks at two-theta positions 13.9°±0.2°, 15.0°±0.2°, 18.3°±0.2°, 19.1°±0.2° and 19.9°±0.2°.

Intensity variations can occur due to processes that influence intensities, in particular the processing history of the sample.

The present invention relates as well to mixtures of two or more crystalline forms of the compound of formula (I), and mixtures of one or more crystalline forms of the compound of formula (I) and the amorphous form of the compound of formula (I).

The present invention further relates to processes for preparing the crystalline forms of the compound of formula (I).

In one embodiment, there is provided a process for preparing Form I comprising:
a) dissolving compound of formula (I) in a $C_{1-4}$alkanol, in particular in 1-butanol or 2-propanol while heating at the reflux temperature of the solvent; and
b) allowing the solution obtained in a) to cool to a temperature below 60° C., such as in the range of from 60° C. to room temperature, in particular below 40° C., such as in the range of from 40° C. to room temperature, more in particular to room temperature In one embodiment, there is provided a process for preparing Form I comprising:
c) dissolving compound of formula (I) in a $C_{1-4}$alkanol, in particular in 1-butanol or 2-propanol while heating at the reflux temperature of the solvent; and
d) allowing spontaneous cooling.

In another embodiment, there is provided a process for preparing Form I comprising:
slurrying Form II in an alcoholic solvent selected from a $C_{1-4}$alkanol, in particular from 2-propanol, ethanol, 1-butanol, methanol, a mixture of alcohol (such as methanol, ethanol, propanol, isopropanol, 1-butanol, or 2-butanol) and dichloromethane or water, or a mixture thereof, at the reflux temperature of the alcoholic solvent; or slurrying a mixture of Form I and Form II in a solvent selected from a $C_{1-4}$alkanol, in particular ethanol, 2-propanol, 1-butanol, methanol, or from methyl isopropylketone (MIK), THF, acetonitrile, acetone, 1-methoxypropan-2-ol (1-M-2-P), methyl ethylketone (MEK), dichloromethane, a mixture of alcohol in particular a $C_{1-4}$alkanol mixture (such as methanol, ethanol, propanol, isopropanol, 1-butanol, or 2-butanol) and dichloromethane or water, or a mixture thereof, at a temperature of at least about 30° C., in particular of at least about 50° C., such as in the range of from 30° C. to room temperature to 60° C., or in the range of from 40° C. to the reflux temperature of the mixture.

In another embodiment, there is provided a process for preparing Form II comprising:
a) preparing a suspension of the amorphous form of the compound of formula (I) in a $C_{1-4}$alkanol, in particular in 2-propanol;
b) stirring the suspension at room temperature; and
c) seeding the suspension with crystal seeds of Form II or Form I.

In another embodiment, there is provided an alternative process for preparing Form II comprising:
a) dissolving compound of formula (I) in a $C_{1-4}$alkanol, in particular in 2-propanol; and
b) keeping the solution from step a) at room temperature during at least 1 day, such as a time period ranging between 1 day and 4 days, or 1 day and 2 days, or at around 0° C. during at least 4 hours, such as a time period ranging between 4 hours and 24 hours, or between 4 hours and 12 hours, or between 4 hours and 8 hours.

In other embodiments, there are provided processes for preparing Forms III, IV, V, and VI.

The present invention also relates to a crystalline form of the compound of formula (I) for use as a medicament. This invention also relates to a crystalline form of the compound of formula (I) for use as a HCV inhibitor, or for use in the treatment of HCV-related conditions. The invention also relates to the use of a crystalline form of the compound of formula (I) in the manufacture of a medicament for inhibiting HCV, or for the treatment of HCV-related conditions. The invention furthermore provides a method of treating a mammal suffering from HCV-related conditions comprising administering an effective amount of the crystalline forms of the compound of formula (I), mixtures thereof, to said mammal. The mammal preferably is a human. In one embodiment, the crystalline form in the above mentioned uses and methods is selected from Form I, II, III, IV, V, and VI, including mixtures thereof.

Furthermore, the invention provides a pharmaceutical composition comprising a crystalline form of the compound of formula (I), or in particular a form selected from Form I, II, III, IV, V, and VI, including mixtures thereof, and a pharmaceutically acceptable carrier. The said crystalline form of the compound of formula (I) preferably is present in an effective amount, i.e. an amount that is effective in preventing or treating HCV infection or conditions associated with HCV infection.

Further provided are crystal seeds of Form I, Form II, or a mixture of the amorphous form of the compound of formula (I) and Form II, which each are useful in the preparation of Form II of the compound of formula (I).

In one embodiment, the invention provides the polymorphic forms designated Form I, Form II, Form III, Form IV, Form V, and Form VI, of the compound of formula (I), as specified above, substantially free from impurities. In a particular embodiment, these forms contain no more than 10% of impurities, or no more than 5% of impurities, or no more than 1% of impurities, or no more than 0.5% of impurities, or no more than 0.1% of impurities. The impurities may be other compounds or may be any of the other solid forms of the compound of formula (I), in particular other polymorphic forms or the amorph form. Polymorphic purity may be tested by XPRD, with the area under the peaks used to calculate polymorphic purity.

The present invention further provides a mixture of two or more crystalline forms of the compound of formula (I), wherein the crystalline forms are selected from Form I, Form II, Form III, Form IV, Form V, and Form VI. In one embodiment, there is provided a mixture comprising Form II and Form I of the compound of formula (I). In another embodiment, there is provided a mixture comprising Form III and Form II of the compound of formula (I).

This invention further provides a mixture of one or more crystalline forms of the compound of formula (I) and the amorphous form of the compound of formula (I), wherein the crystalline forms are selected from Form I, Form II, Form III, Form IV, Form V, and Form VI. In one embodiment, there is provided a mixture comprising Form II and the amorphous form of the compound of formula (I). This mixture of Form II and the amorphous form of the compound of formula (I) is, in particular, useful as seeding material for preparing Form II.

The characterising XPRD intensity peak positions (in degrees 2-theta) of each of the forms are shown in the following table 1. The most characterizing XPRD intensity peak positions of each form are marked in bold.

TABLE 1

XPRD intensity peak positions of the polymorphic forms of the compound of formula (I)

| | Form I | Form II | Form III | Form IV | Form V | Form VI |
|---|---|---|---|---|---|---|
| XPRD intensity peaks (±0.2° 2-theta) | 6.5° | 4.6° | 6.5° | 5.6° | 9.6° | 4.4° |
| | 8.5° | 6.5° | 9.8° | 9.6° | 19.0° | 9.9° |
| | 10.7° | 10.2° | 13.7° | 11.8° | — | 10.5° |
| | 13.7° | 12.9° | 14.8° | 13.0° | — | 12.9° |
| | 14.8° | 14.4° | 17.8° | 15.9° | — | 16.5° |
| | 17.1° | 20.4° | — | 17.1° | — | — |
| | 18.6° | — | — | — | — | — |

Figure 4:
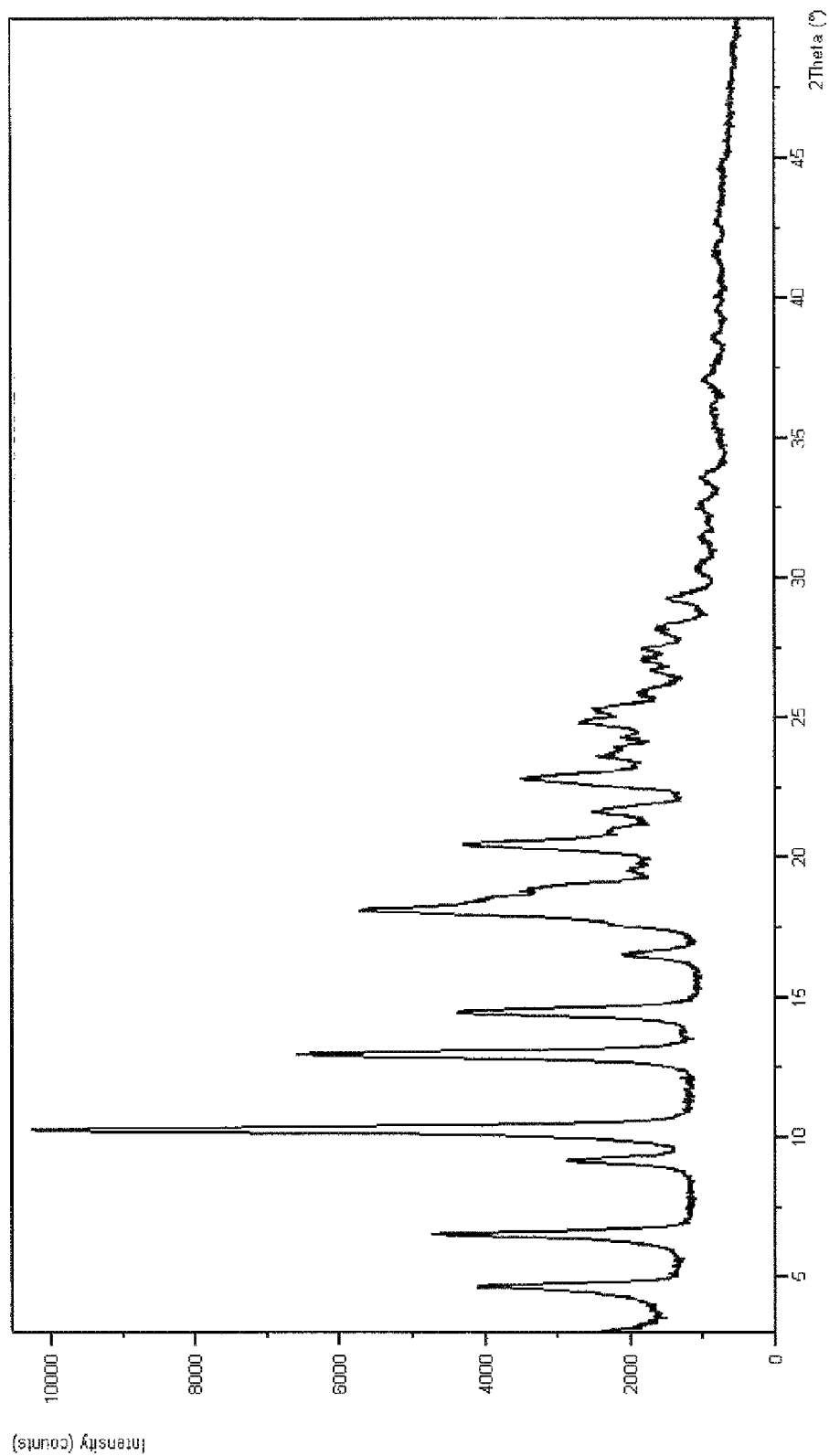
FIG. 4 is an XPRD pattern representation of Form II
Figure 7:
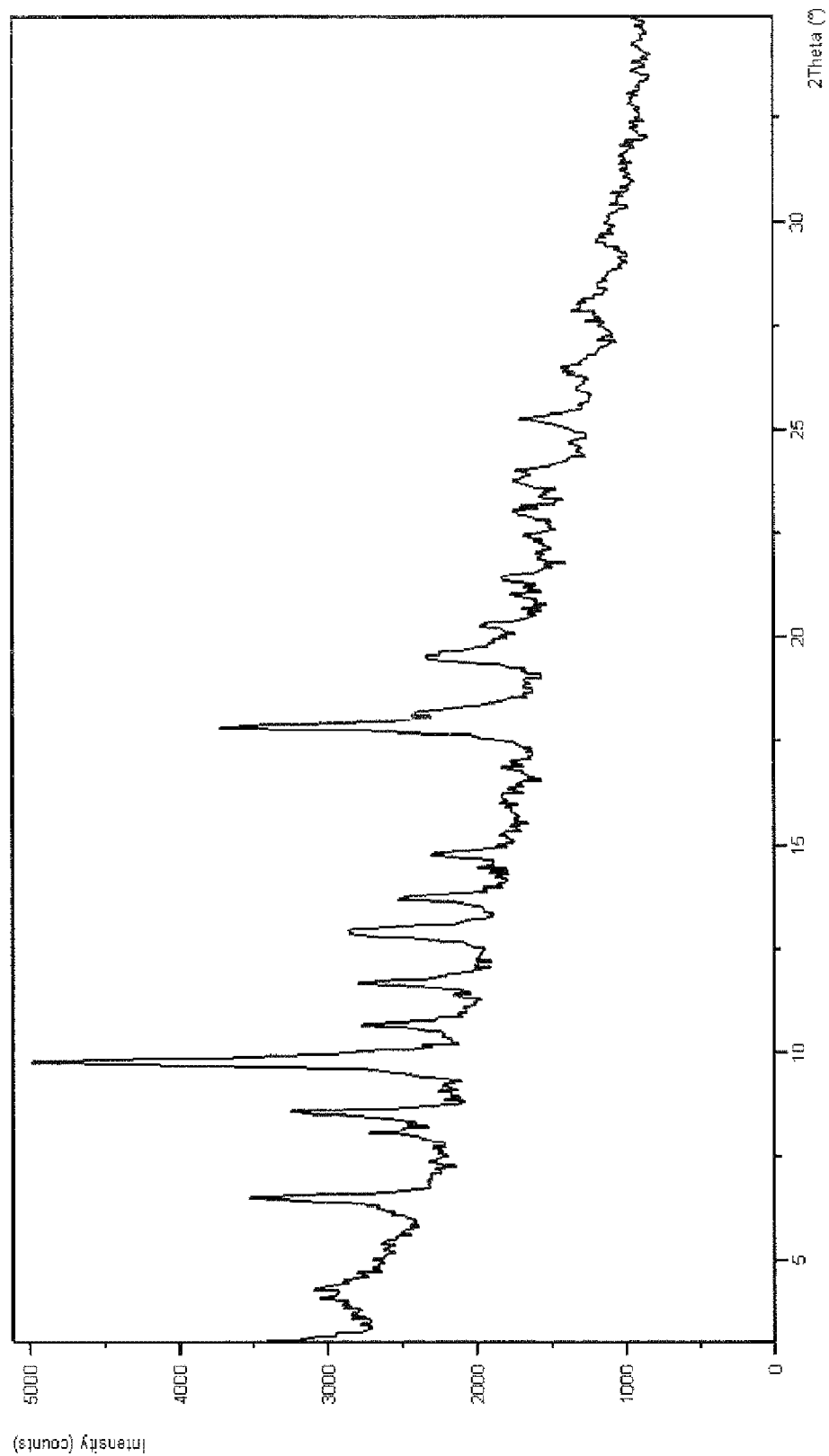
FIG. 7 is an XPRD pattern representation of Form III
Figure 10:
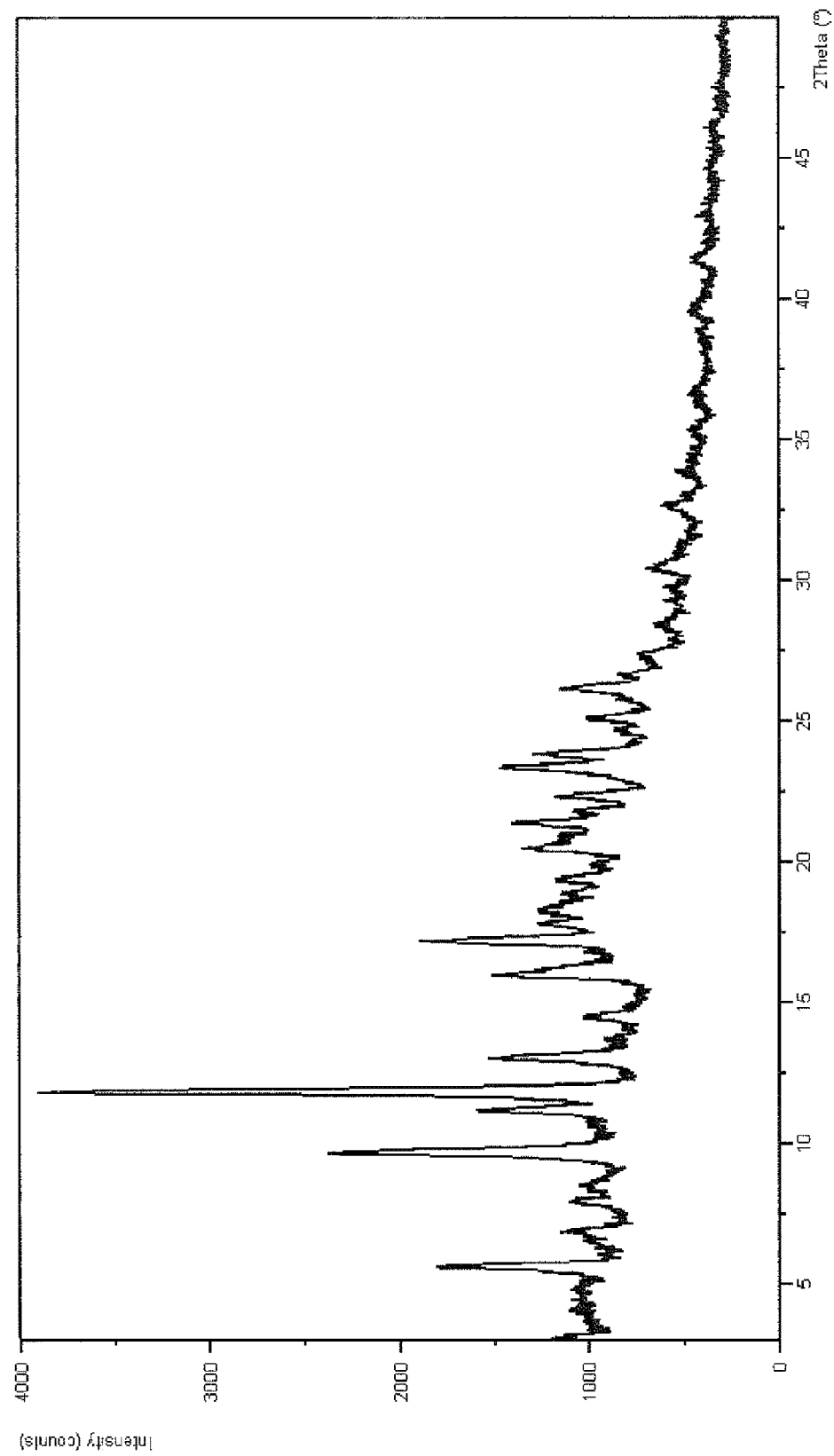
FIG. 10 is an XPRD pattern representation of Form IV
Figure 13:
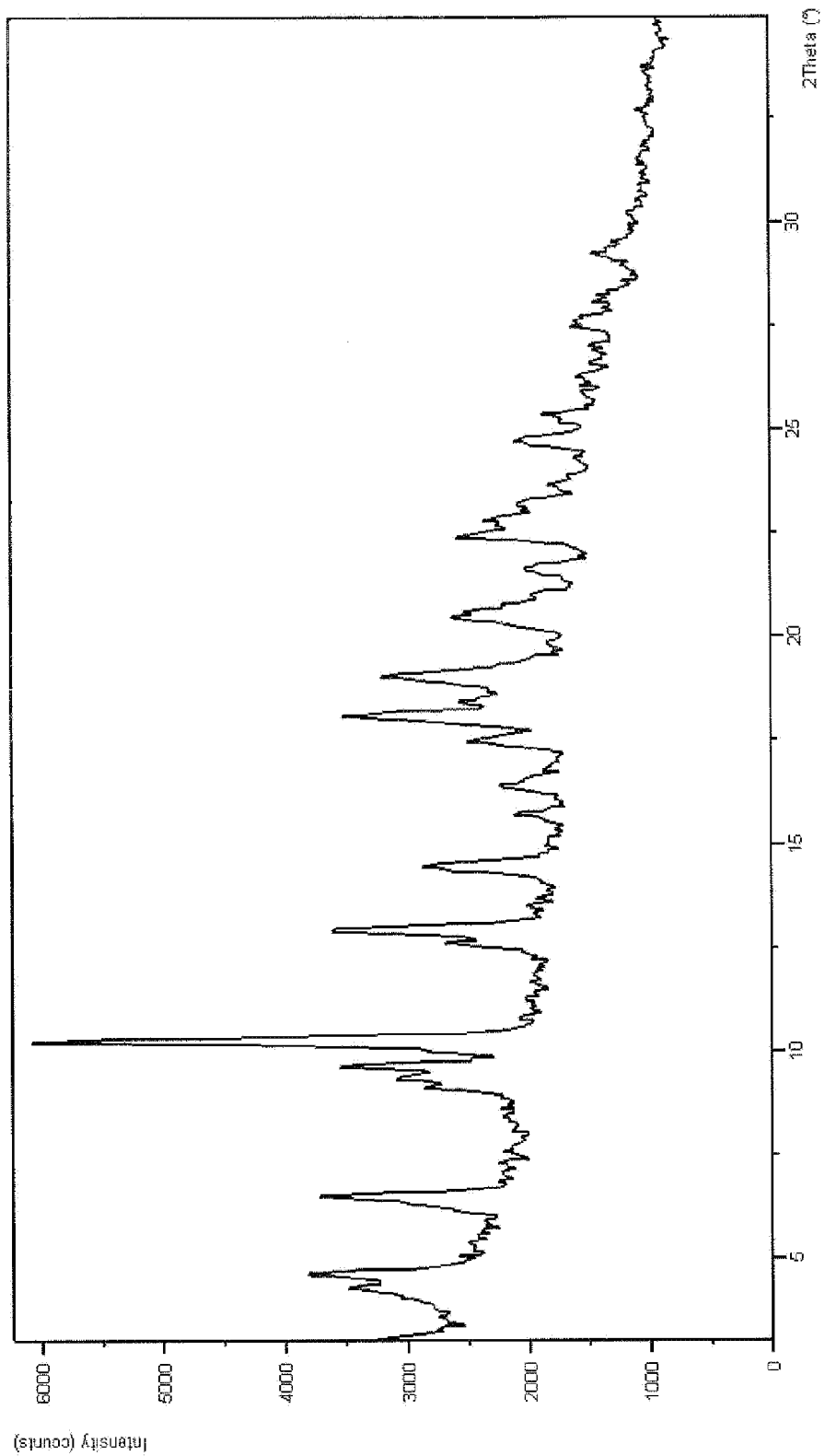
FIG. 13 is an XPRD pattern representation of Form V
Figure 14:
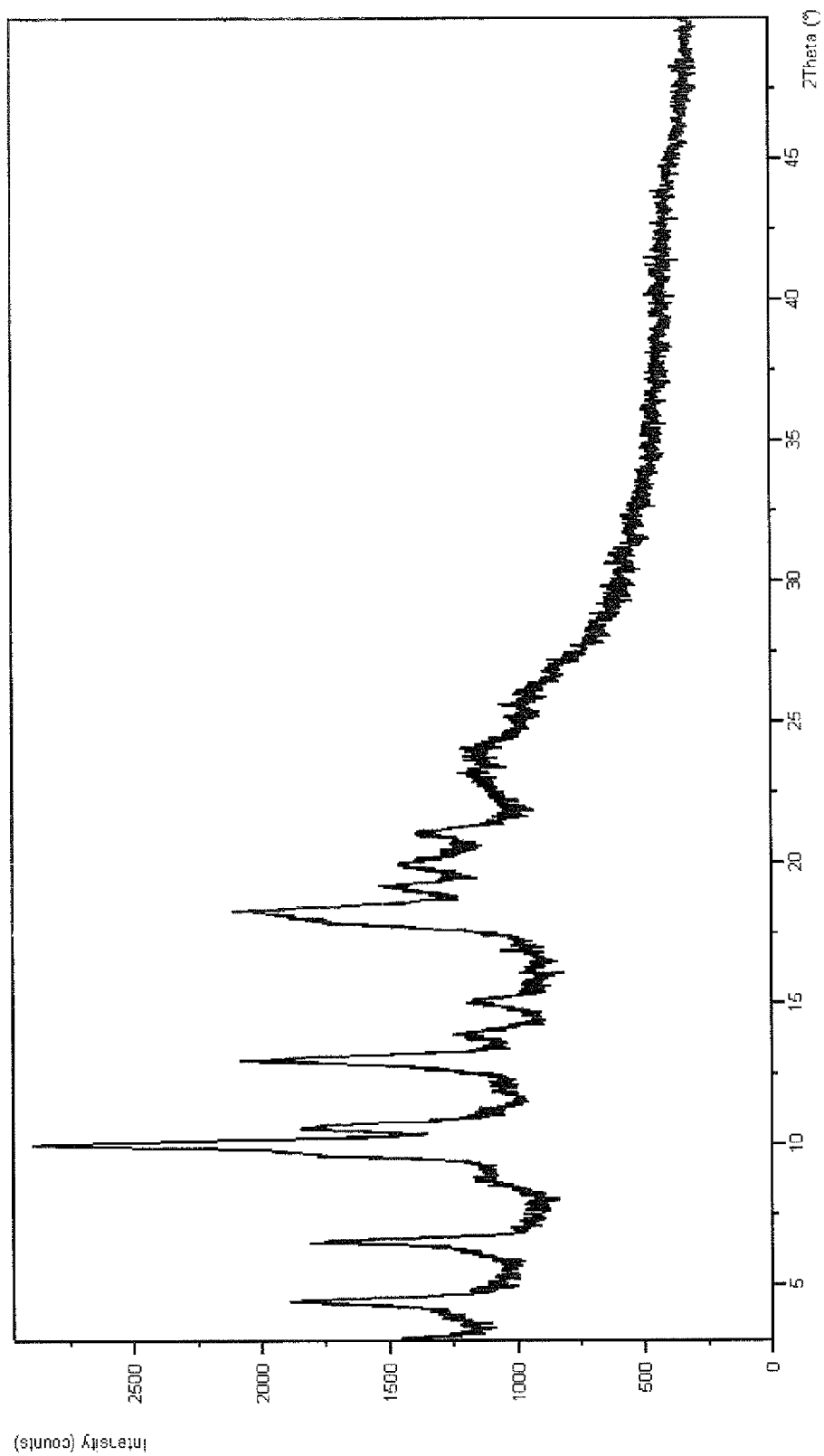
FIG. 14 is an XPRD pattern representation of Form VI
Figure 15:
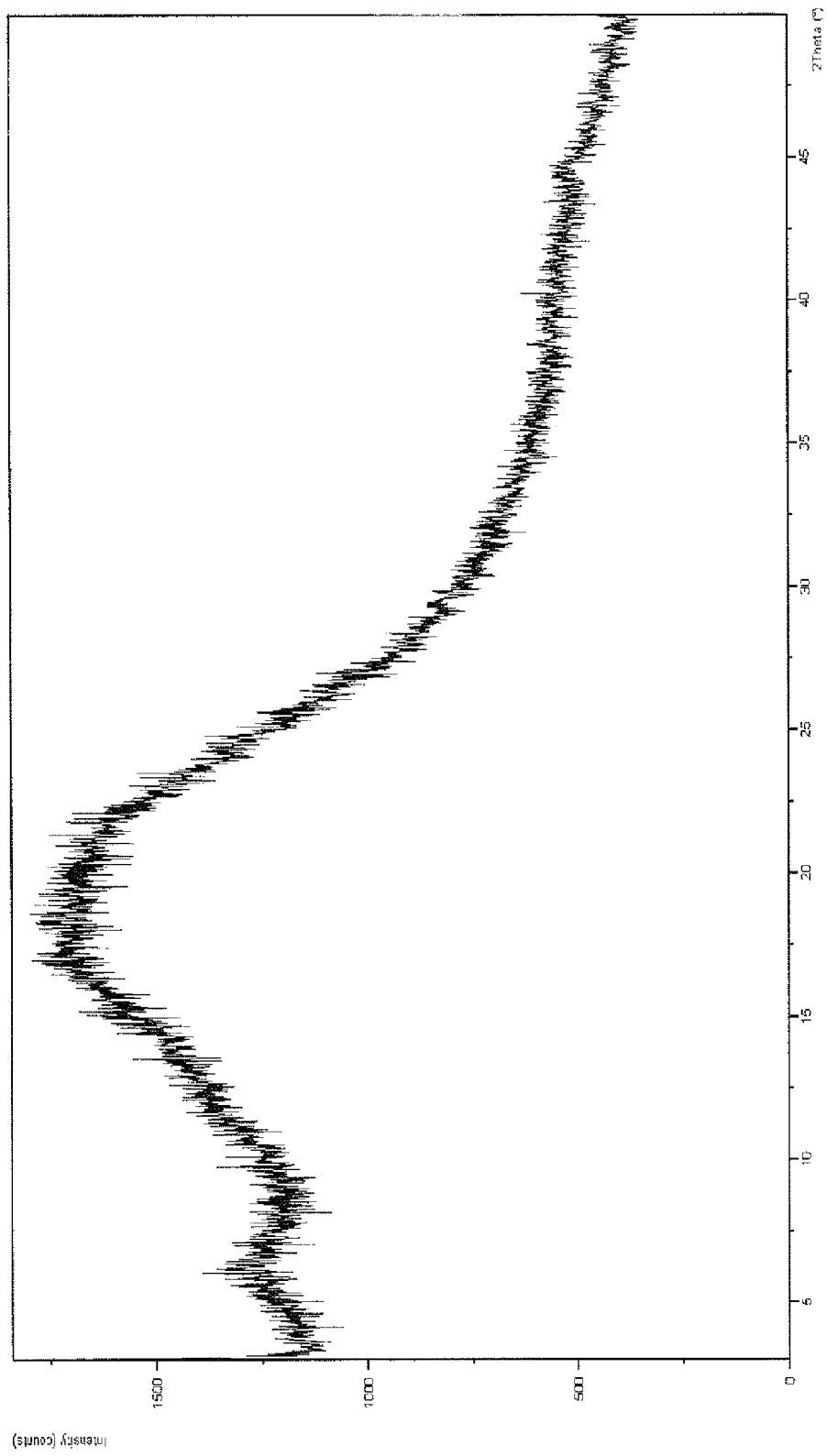
FIG. 15 is an XPRD pattern representation of the compound of formula (I) in amorphous form

The X-ray powder diffraction pattern of Form I is as substantially depicted in FIG. 1. The X-ray powder diffraction pattern of Form II is as substantially depicted in FIG. 4. The X-ray powder diffraction pattern of Form III is as substantially depicted in FIG. 7. The X-ray powder diffraction pattern of Form IV is as substantially depicted in FIG. 10. The X-ray powder diffraction pattern of Form V is as substantially depicted in FIG. 13. The X-ray powder diffraction pattern of Form VI is as substantially depicted in FIG. 14.

The XPRD data and pattern representations of all forms I-VI can be obtained using a Philips X'PertPRO MPD diffractometer PW3050/60 with a generator PW3040. The instrument was equipped with a Cu LFF X-ray tube PW3373/00. The compound to be analysed was spread on a zero background sample holder. The instrument parameters were as follows:

| | |
|---|---|
| generator voltage: | 45 kV |
| generator amperage: | 40 mA |
| geometry: | Bragg-Brentano |
| stage: | spinner stage. |

The scanning parameters for Forms I, II, III, and IV were as follows: the range was 3° to 50° 2-theta with a continuous scan at a rate of 0.01675°/step, at 29.845 sec/step. The spinner revolution time was 1 sec, the radiation type CuKα, and the radiation wavelength was 1.54056 Å.

The scanning parameters for Forms V and VI were as follows: the range was 3° to 35° 2-theta with a continuous scan at a rate of 0.0502448°/step, at 90.17 sec/step. The spinner revolution time was 1 sec, the radiation type CuKα, and the radiation wavelength was 1.54056 Å. The Incident beam path parameters for Forms I, II, III, IV, V, and VI were as follows:

| | |
|---|---|
| program. divergence slit: | 15 mm |
| Soller slit: | 0.04 rad |
| beam mask: | 15 mm |
| anti scatter slit: | 1° |
| beam knife: | + |

The diffracted beam path parameters for Forms I, II, III, IV, V, and VI were as follows:

| | |
|---|---|
| long anti scatter shield: | + |
| Soller slit: | 0.04 rad |
| Ni filter: | + |
| detector: | X'Celerator |

The accuracy of the XPRD peak positions provided for Forms I, II, III, IV, V, and VI is defined as 0.2° due to experimental differences, such as instrumentations, sample preparations, and the like.

The characterising IR absorbance peak positions (in wavenumbers $cm^{-1}$) of Forms I, II, III, and IV are shown in the following table 2. The most characterizing IR absorbance peak positions of each form are marked in bold.

TABLE 2

IR absorbance peak positions of the polymorphic forms of the compound of formula (I)

| | Form I | Form II | Form III | Form IV |
|---|---|---|---|---|
| IR absorbance peaks in wavenumbers, in $cm^{-1}$ (±1 $cm^{-1}$) | 3405 | 1592 | 3120 | 1713 |
| | 3066 | 1066 | 2870 | 1598 |
| | 1712 | 1037 | 1717 | 1369 |
| | 1596 | 881 | 1664 | 1039 |
| | 1517 | 873 | 1598 | 884 |
| | 1454 | — | 1353 | 872 |
| | 1427 | — | 1076 | 846 |
| | 1351 | — | 1063 | — |
| | 1301 | — | 1039 | — |
| | 1285 | — | 881 | — |
| | 1132 | — | — | — |
| | 1111 | — | — | — |
| | 1149 | — | — | — |
| | 1072 | — | — | — |
| | 975 | — | — | — |
| | 956 | — | — | — |
| | 881 | — | — | — |
| | 872 | — | — | — |
| | 800 | — | — | — |

Figure 2:
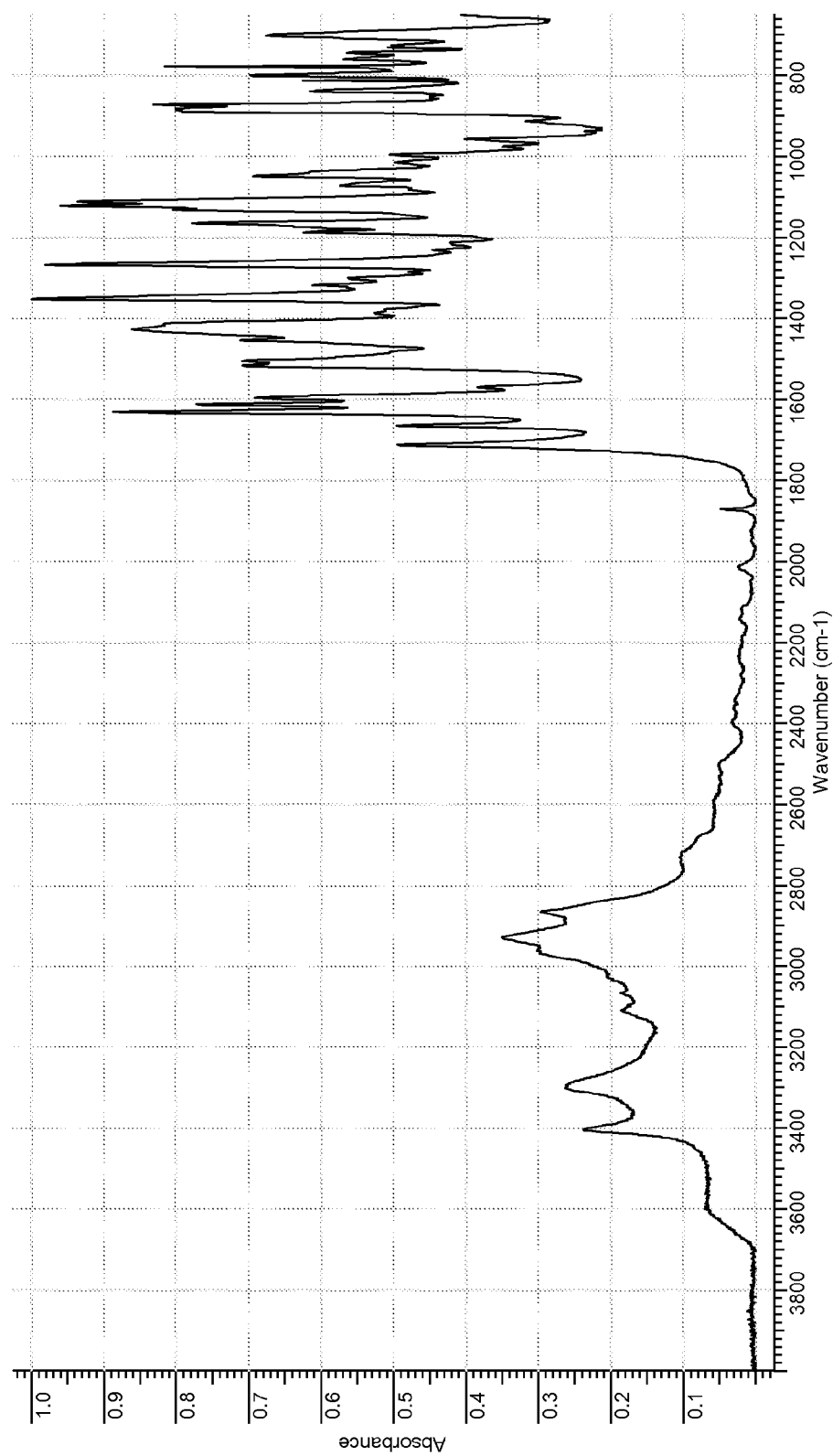
FIG. 2 is an Infrared (IR) spectrum representation of Form I
Figure 5:
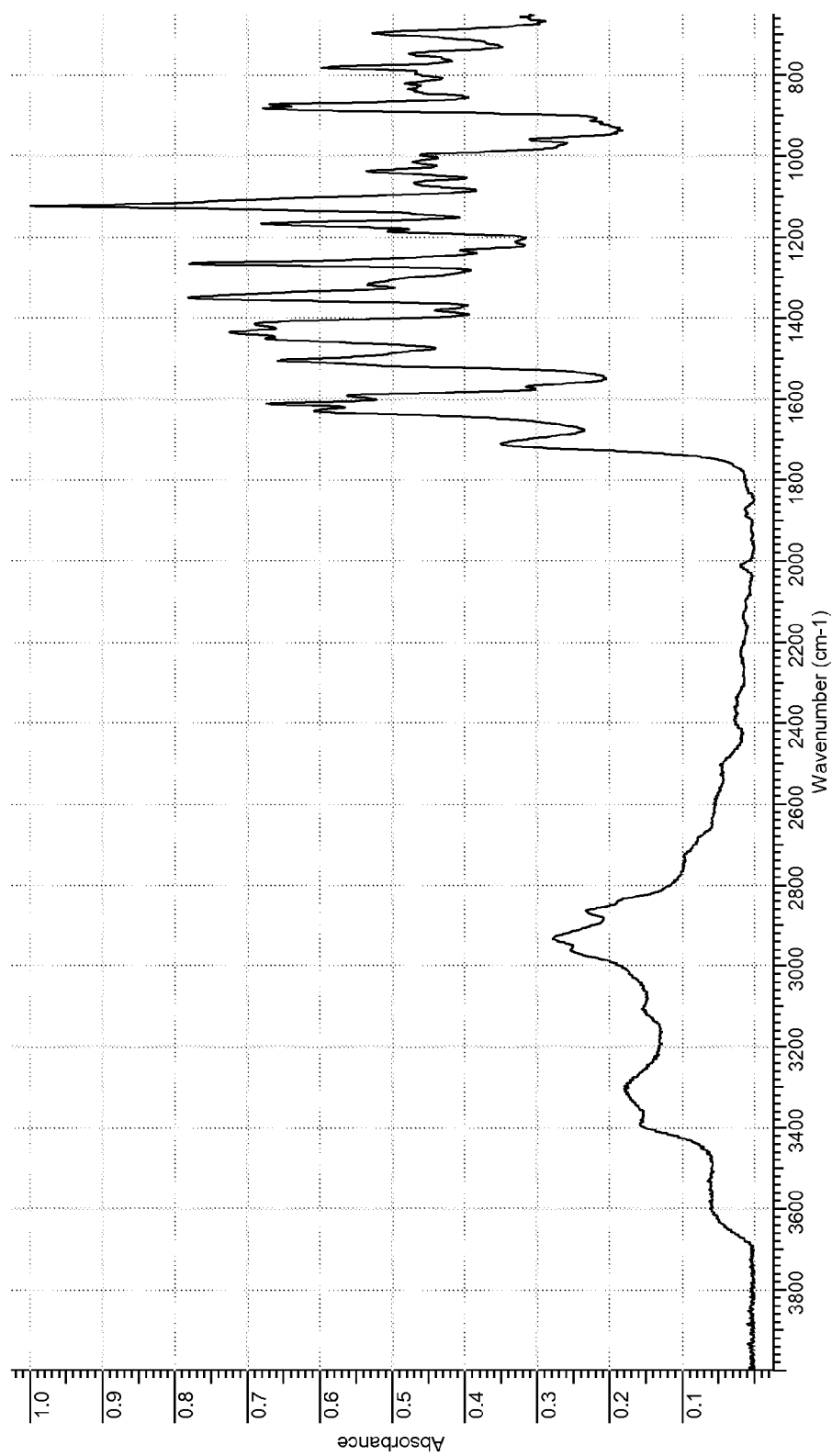
FIG. 5 is an IR spectrum representation of Form II
Figure 8:
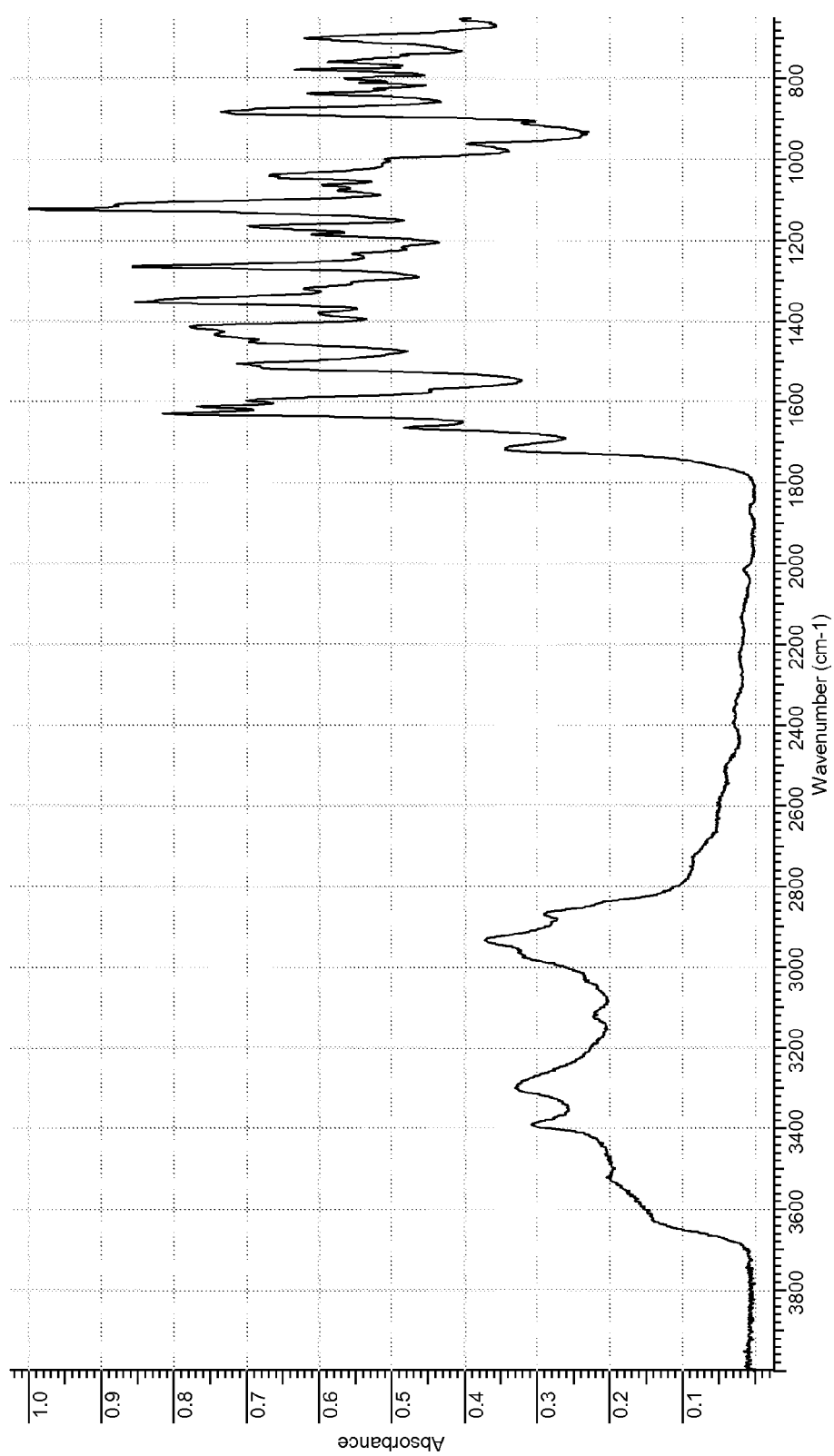
FIG. 8 is an IR spectrum representation of Form III
Figure 11:
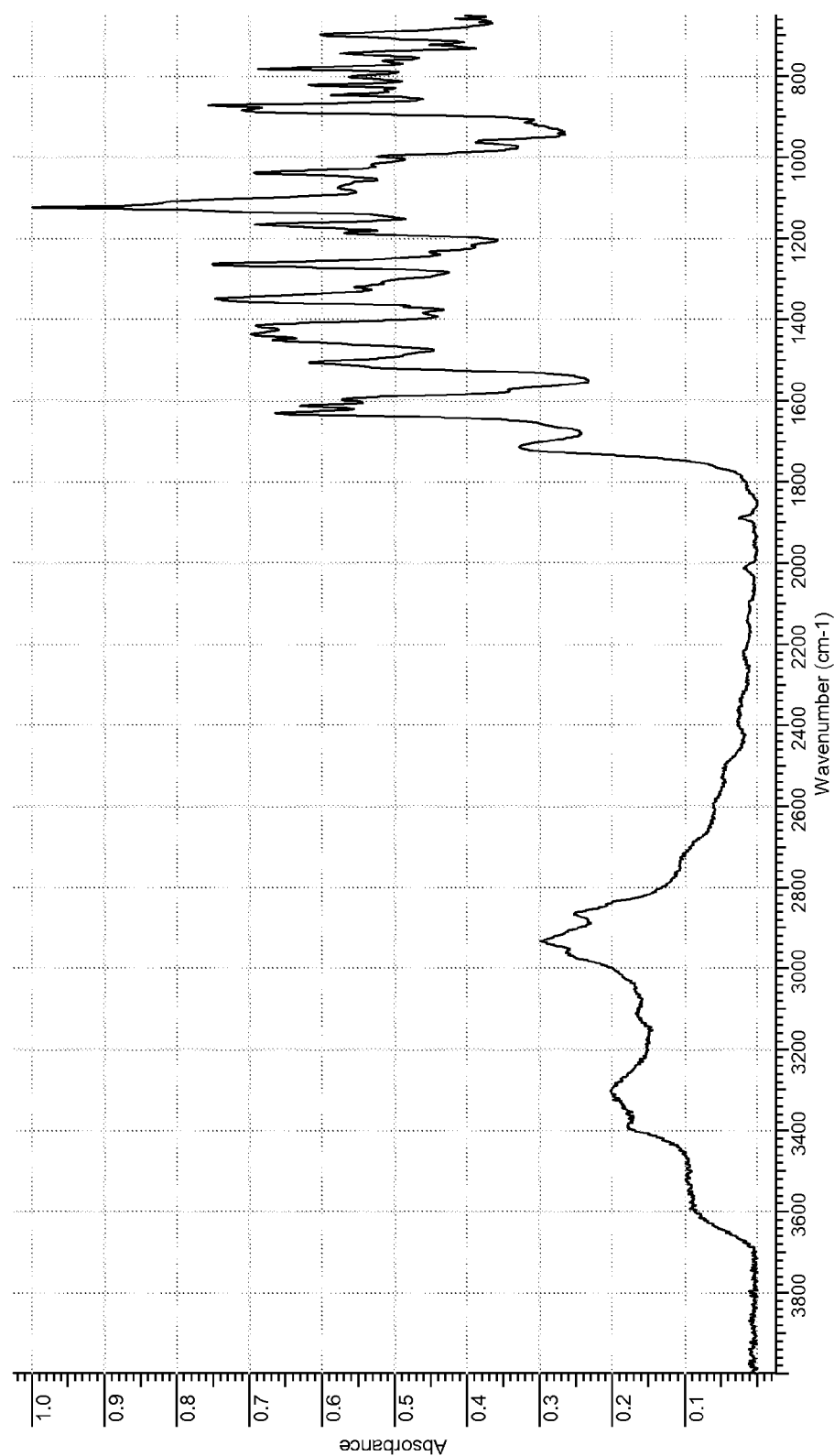
FIG. 11 is an IR spectrum representation of Form IV

The IR pattern of Form I is as substantially depicted in FIG. 2. The IR pattern of Form II is as substantially depicted in FIG. 5. The IR pattern of Form III is as substantially depicted in FIG. 8. The IR pattern of Form IV is as depicted in FIG. 11.

The IR data and pattern representations were obtained using infrared spectrometry micro Attenuated Total Reflectance (microATR) with a Nexus FTIR spectrophotometer. The micro ATR accessory was a Harrick Split Pea with Si crystal. The detector used was a DTGS with KBr windows. The scan parameters for Forms I, II, III, and IV were as follows:

| | |
|---|---|
| number of scans: | 32 |
| resolution: | 1 cm$^{-1}$ |
| wavelength range: | 4000 to 400 cm$^{-1}$ |
| baseline correction: | yes |
| beamsplitter: | Ge on KBr. |

The accuracy of the IR absorbance peaks provided for Forms I, II, III, and IV is defined as 1 cm$^{-1}$ due to experimental differences, such as instrumentations, sample preparations, and the like.

The characterizing DSC endothermic peak positions or ranges (in ° C.) of Forms I, II, III, and IV are shown in the following table 3.

TABLE 3

DSC endothermic peak positions or ranges of the polymorphic forms of the compound of formula (I)

| | Form I | Form II | Form III | Form IV |
|---|---|---|---|---|
| DSC endothermic peaks (in ° C.) | 259.5 | 194.4 | 211.6 | 221.2 |

Figure 3:
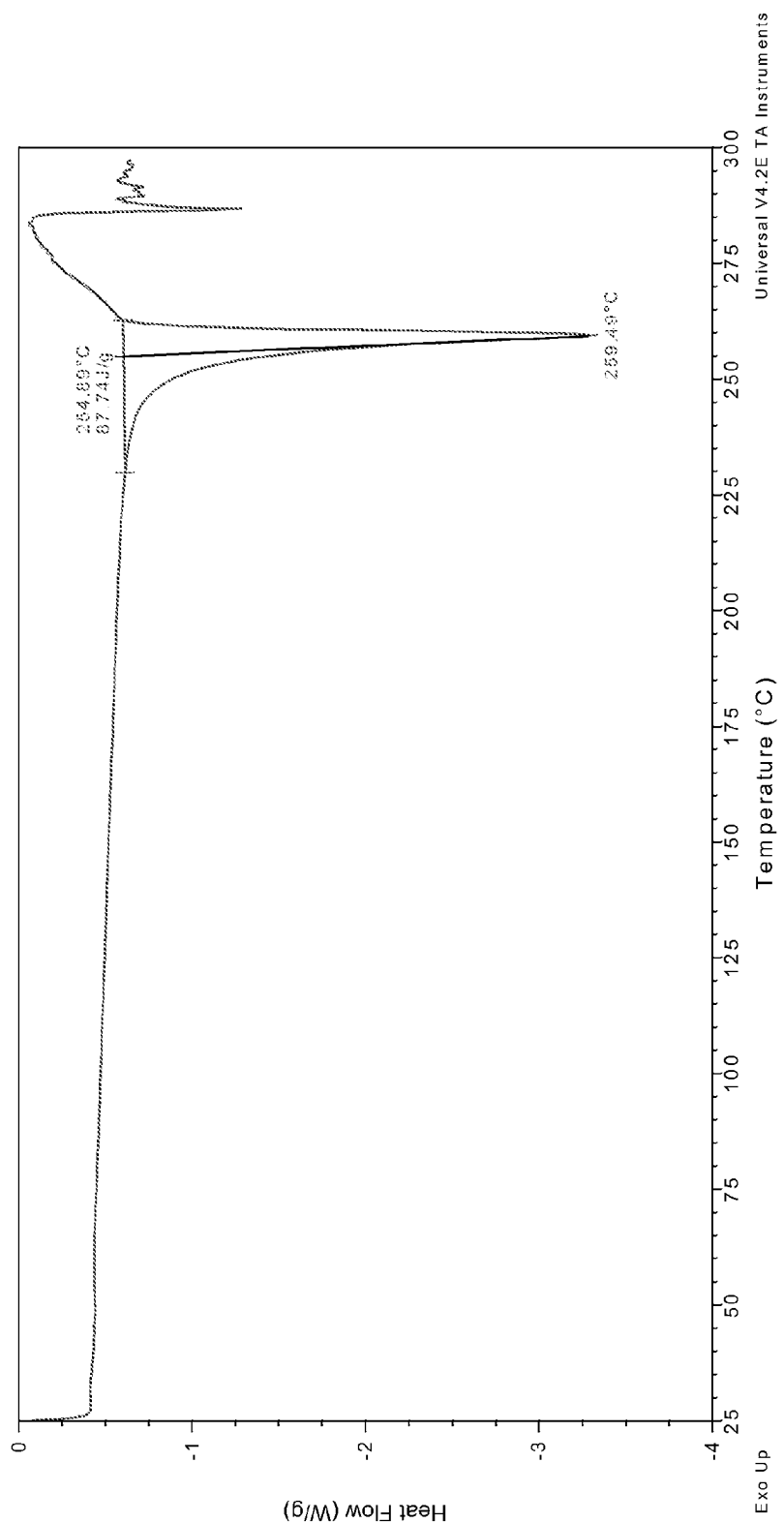
FIG. 3 is a Differential Scanning Calorimetry (DSC) curve of Form I
Figure 6:
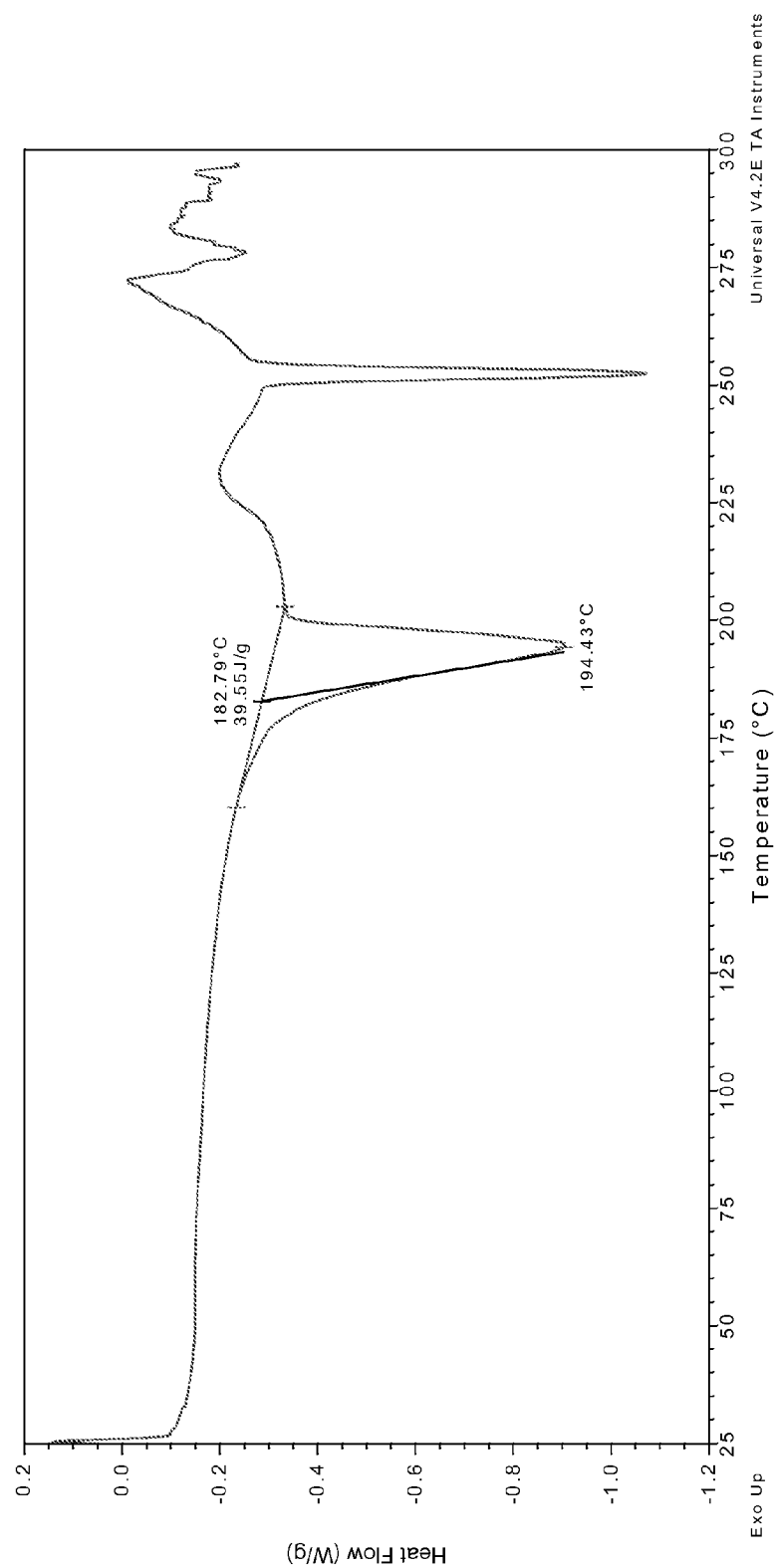
FIG. 6 is a DSC curve of Form II
Figure 9:
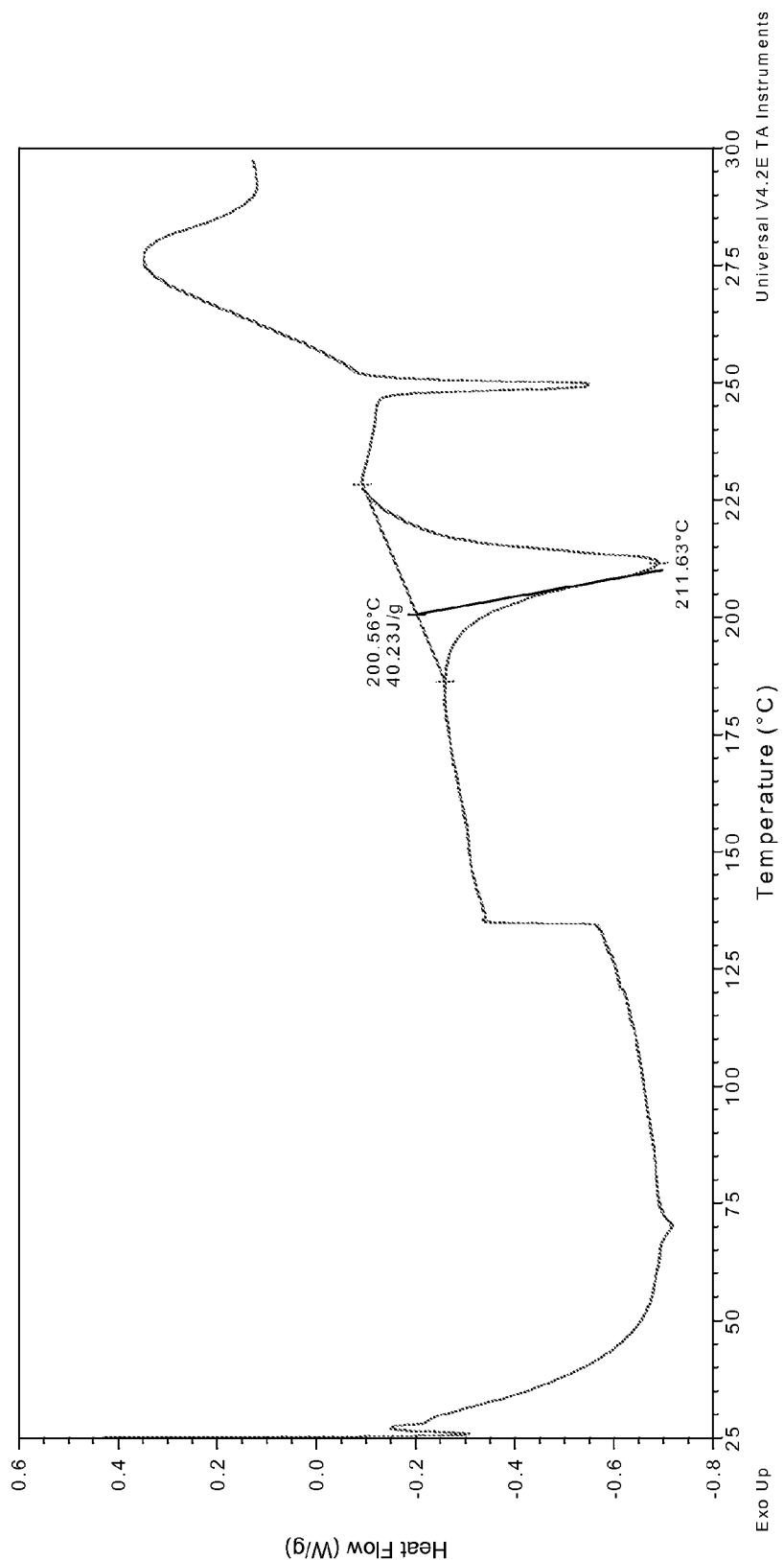
FIG. 9 is a DSC curve of Form III
Figure 12:
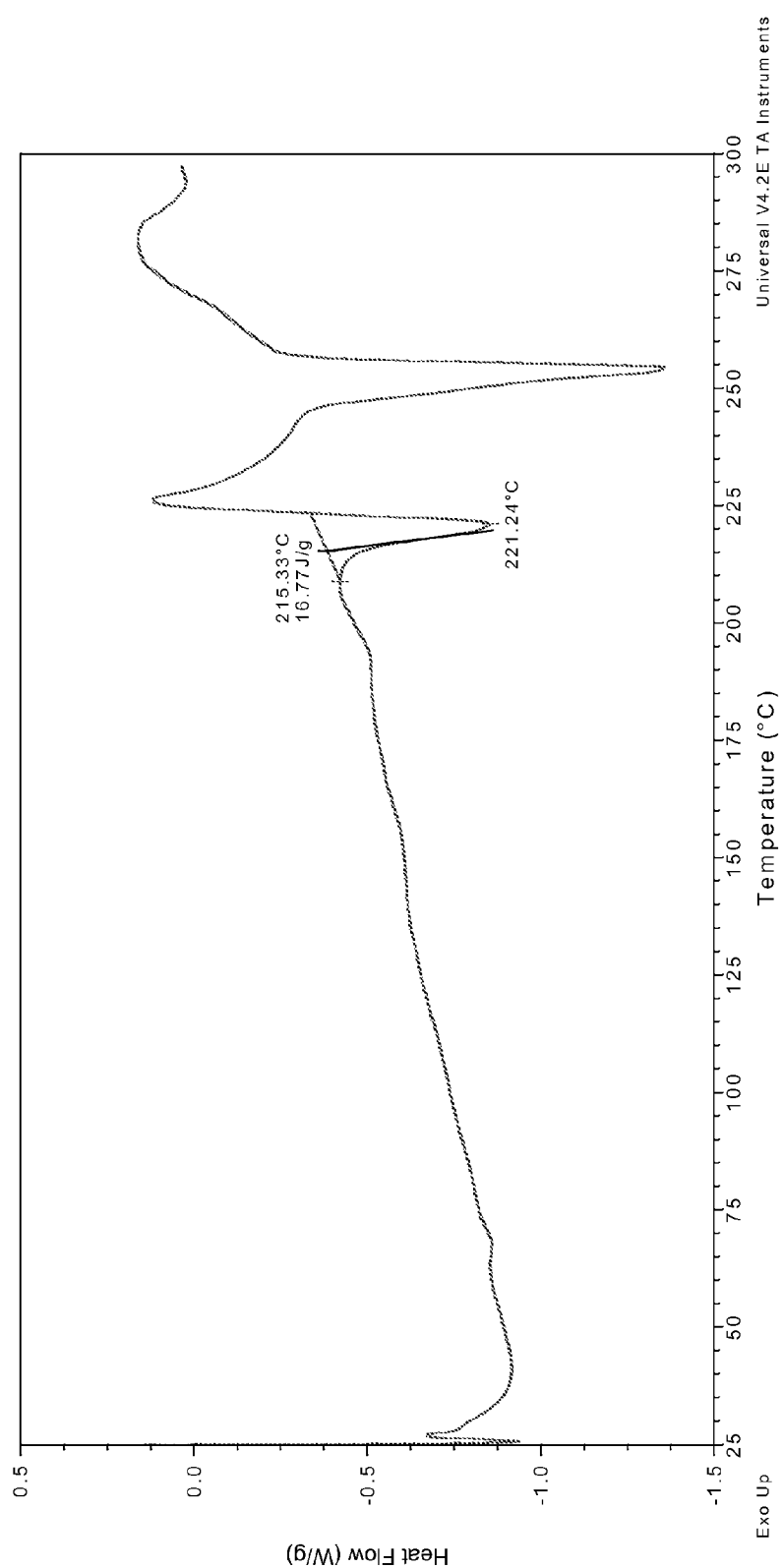
FIG. 12 is a DSC curve of Form IV

The DSC curve of Form I is as substantially depicted in FIG. 3. The DSC curve of Form II is as substantially depicted in FIG. 6. The DSC curve of Form III is as substantially depicted in FIG. 9. The DSC curve of Form IV is as substantially depicted in FIG. 12.

The DSC data and curve representations were obtained using a TA-Instruments Q1000 MTDSC equipped with a RCS cooling unit. The weight of the samples was about 3 mg, which were transferred into a standard aluminum TA-Instrument sample pan. The samples were scanned at a rate of 10° C./min from 25° C. to a final temperature of 300° C. The oven was constantly purged with nitrogen gas at a flow rate of 50 ml/min.

The tolerance of the DSC curves provided for Forms I and II is defined as 3° C. due to experimental differences, such as instrumentation, sample preparation, and the like.

Polymorph Form I was found to be the most stable form. It moreover is the least hygroscopic form. This makes Form I particularly attractive for use as active ingredient in pharmaceutical dosage forms.

Polymorph Form II was found to be less stable but nevertheless sufficiently stable to be used in pharmaceutical dosage forms. Its intrinsic dissolution was found to be greater than that of Form I. Form II may therefore find use in pharmaceutical dosage forms that are used in situations were a higher intrinsic dissolution is desired. A higher intrinsic dissolution may positively influence the pharmacokinetic properties of the active ingredient of formula (I), e.g. the active ingredient may be more quickly available in the bloodstream or at the location in the body where it has to exert its antiviral activity.

From the DSC data it could be concluded that polymorphs Form I and Form II form a monotropic system. For a monotropic system, a plot of the free energy of the various polymorphs against temperature do not cross before all polymorphs melt—in other words, any transition from one polymorph to another will be irreversible. For an enantiotropic system, a plot of the free energy against temperature shows a crossing point before the various melting points, and it may be possible to convert reversibly between the two polymorphs on heating and cooling.

Preparation of the Crystalline Forms

The compound of formula (I) can be prepared as outlined in the examples.

Form I of the compound of formula (I) can be prepared by a process comprising:
a) dissolving the compound of formula (I) in a $C_{1-4}$alkanol at a temperature comprised between 65° C. and the boiling point of the solution;
b) allowing the solution to cool to room temperature.

As used herein, the term "$C_{1-4}$alkanol" refers to a $C_{1-4}$alkyl alcohol derived from an alkane having from one to four carbon atoms such as methanol, ethanol, 1-propanol, 2-propanol, 1-butanol, 2-butanol, 2-methyl-1-propanol, t.butanol. A subgroup amongst "$C_{1-4}$alkanol" is "$C_{3-4}$alkanol", which are derived from an alkane having from three or four carbon atoms such as 1-propanol, 2-propanol, 1-butanol, 2-butanol, 2-methyl-1-propanol, t.butanol.

Preferred for use in the preparation of Form I are 1-propanol, 2-propanol, 1-butanol, 2-butanol, in particular 1-butanol or 2-propanol. In step a) of the above process for preparing form I, the compound of formula (I) in a $C_{1-4}$alkanol preferably is heated to the reflux temperature of the mixture. In one embodiment, the compound of formula (I) is mixed with the $C_{1-4}$alkanol to form a slurry, and this slurry is heated to reflux temperature of the mixture, whereupon additional $C_{1-4}$alkanol is titrurated to the mixture until a solution is formed. Cooling to room temperature in the above process preferably is slow, e.g. over a period of about 12 h to about 48 h, e.g. over a period of about 12 h, or about 24 h, or about 48 h. In one embodiment, the solution is allowed to cool spontaneously, i.e. without control of the temperature. In another embodiment the solution is allowed to cool with control of temperature. The starting compound of formula (I) in the above process may be any form, such the amorphous or any crystalline form, or mixtures thereof, e.g. a mixture of Form I and Form II.

The amount of 1-butanol or 2-propanol that is added in step a) may be in the range between about 15 and about 25 L/mol, or between about 17 and about 19 L/mol, preferably in a quantity of 17.85 L/mol, or 18.5 L/mol. In one embodiment, the process mentioned above for preparing Form I further comprises, in step b), cooling the solution to 65° C. or higher. In another embodiment, the process mentioned above for preparing Form I further comprises, in step b), partially evaporating the solvent especially in the case when there is no precipitation at 65° C. or higher.

In one embodiment, the present invention provides a process for preparing the crystalline Form I comprising:
a) dissolving compound of formula (I) in 1-butanol or 2-propanol while heating at the reflux temperature of the solvent; and
b) allowing spontaneous cooling to room temperature.

In one embodiment, the process mentioned in the paragraph above for preparing Form I comprises adding 1-butanol in a concentration between 17 and 19 L/mol, preferably in a concentration of 17.85 L/mol, or 18.5 L/mol. In another embodiment, the process mentioned in the latter embodiment for preparing Form I further comprises in step b), applying slow cooling of the solution. In another embodiment, the process mentioned in the latter embodiment for preparing Form I further comprises, in step b), cooling the solution to 65° C. or higher. In another embodiment, the process mentioned in the latter embodiment for preparing Form I further comprises, in step b), partially evaporating the solvent especially in the case when there is no precipitation at 65° C. or higher.

The present invention further provides a slurrying process for preparing the crystalline Form I comprising:
slurrying Form II in an alcoholic solvent, in particular a $C_{1-4}$alkanol, which may be selected from 2-propanol, ethanol, 1-butanol, methanol, a mixture of alcohol, in particular a $C_{1-4}$alkanol, (such as methanol, ethanol, propanol, isopropanol, 1-butanol, or 2-butanol) and dichloromethane or water, or a mixture thereof, at the reflux temperature of the alcoholic solvent; or
slurrying a mixture of Form I and Form II in a solvent selected from a $C_{1-4}$alkanol (in particular 2-propanol, 1-butanol, methanol, ethanol), methyl isopropylketone (MIK), THF, acetonitrile, acetone, 1-methoxypropan-2-ol (1-M-2-P), methyl ethylketone (MEK), dichloromethane, a mixture of alcohol (such as a $C_{1-4}$alkanol such as methanol, ethanol, propanol, isopropanol, 1-butanol, or 2-butanol) and dichloromethane or water, or a mixture thereof, at a temperature in the range of from about 30° C. to the reflux temperature of the mixture, or at a temperature in the range of from about 30° C. to about 100° C., or at a temperature in the range of from about 40° C. to about 80° C., or at a temperature of at least about 30° C.

The slurrying processes for preparing Form I may further comprise, stirring the slurry of Form II at room temperature in an alcoholic solvent, e.g. a $C_{1-4}$alkanol, or the slurry of a mixture of Form I and Form II in a solvent as indicated above.

The slurrying processes for preparing Form I may further comprise stirring during a period of from about 2 hours to about 24 hours, or from about 2 hours to about 12 hours, in one embodiment during a period of at least 2 hours, the slurry of Form II in an alcoholic solvent, or the slurry of a mixture of Form I and Form II in a solvent as indicated above. The stirring may be performed during at least 4 hours, e.g. during at least 8 hours.

The slurrying processes for preparing Form I may further comprise filtering the precipitates obtained after slurrying Form II in an alcoholic solvent, or after slurrying a mixture of Form I and Form II in a solvent as indicated above.

The slurrying processes for preparing Form I may further comprise, after the filtering step of the paragraph above, washing the filtered precipitates obtained after slurrying Form II in an alcoholic solvent, or after slurrying a mixture of Form I and Form II in a solvent as indicated above, wherein the washing step is performed with the same solvent employed during the slurrying step.

In the preparation of any of the solid Forms of the present invention, which proceeds from a clear solution of the compound of formula (I), the solid form of the starting material has no influence on the solid form of the end product and control of the resulting solid form is performed via the control of the process parameters.

The invention also provides a process for preparing Form II comprising:
a) preparing a suspension of the amorphous form of the compound of formula (I) in a $C_{1-4}$alkanol, in particular in 2-propanol and;
b) stirring the suspension at room temperature; and
c) seeding the suspension with crystal seeds of Form II or Form I.

In case the seeding process of step c) above is performed with crystal seeds of Form I, Form II will be obtained with a minimal content of Form I.

In one embodiment, the process for preparing Form II further comprises, after step c), stirring the seeded suspension at room temperature.

The process for preparing Form II may further comprise, after step c), stirring the seeded suspension during 15 minutes to 72 hours. The stirring may be performed during 5 to 60 hours, in particular during 10 to 48 hours.

The process for preparing Form II may further comprise filtering the precipitate obtained after step c). The process for preparing Form II may further comprise, after the filtering step of the paragraph above, washing the filtered precipitate obtained after step c) with isopropanol.

This invention also provides an alternative process for preparing Form II comprising:
a) dissolving compound of formula (I) in a $C_{1-4}$alkanol, in particular in 2-propanol; and
b) keeping the solution from step a) at room temperature during at least 1 day, in particular a time period in the range of about 1 day to about 4 days, or in the range of about 1 day to about 2 days; or at around 0° C. during at least 4 hours, in particular a time period in the range of about 4 hours to about 12 hours.

In one embodiment, the alternative process above for preparing Form II comprises, prior to step a), dissolving compound of formula (I) in dichloromethane, thereafter adding the $C_{1-4}$alkanol, in particular adding the 2-propanol as prescribed in step a), and before step b), eliminating partially or completely the dichloromethane. Elimination of the dichloromethane may be performed by evaporation using for instance a rotavapor under vacuum.

In another embodiment, the alternative process above for preparing Form II comprises keeping the solution from step a) at room temperature during a time period comprised between about 5 h and about 48 h, in particular during a time period comprised between about 14 h and about 36 h. The alternative process above for preparing Form II may comprise keeping the solution from step a) at room temperature during at least 14 h, 16 h, 18 h, 20 h, 22 h, 24 h, 26 h, 28 h, 30 h, 32 h, 34 h, or 36 h.

In another embodiment, the alternative process above for preparing Form II comprises keeping the solution from step a) at around 0° C. during a time period comprised between about 5 h and about 48 h, in particular during a time period comprised between about 5 h and about 36 h, more in particular during a time period comprised between about 5 h and about 16 h. The alternative process above for preparing Form II may comprise keeping the solution from step a) at around 0° C. during at least 5 h, 6 h, 7 h, 8 h, 9 h, 10 h, 11 h, 12 h, 13 h, 14 h, 15 h, or 16 h.

The alternative process above for preparing Form II may also comprise keeping the solution from step a) at a temperature comprised between −10° C. and 10° C., in particular at a temperature comprised between −5° C. and 5° C., e.g at a temperature of −10° C., −9° C., −8° C., −7° C.; −6° C., −5° C., −4° C., −3° C.; −2° C., −1° C., 0° C., 1° C., 2° C., 3° C., 4° C., 5° C., 6° C., 7° C., 8° C., 9° C., or 10° C., during at least 4 h, in particular a time period in the range of about 4 hours to about 12 hours.

In another embodiment, the alternative process above for preparing Form II comprises in step b) stirring the solution while keeping it or maintaining it at room temperature during at least 1 day, in particular a time period in the range of about 1 day to about 4 days, or in the range of about 1 day to about 2 days; or at around 0° C. during at least 4 hours, in particular a time period in the range of about 4 hours to about 12 hours.

The invention also provides a process for preparing Form III comprising:

a) preparing a saturated or nearly saturated solution of the compound of formula (I) in acetonitrile, and a saturated or nearly saturated solution of the compound of formula (I) in water;
b) heating the two saturated or nearly saturated solutions from step a) at least 40° C.;
c) mixing the two saturated or nearly saturated solutions from step b) in a 50/50 volume ratio.

In one embodiment, the process for preparing Form III comprises, in step b), heating the two saturated or nearly saturated solutions at about 40° C. to about 70° C., preferably at about 45° C. to 65° C., more preferably at about 50° C. to 60° C. The process for preparing Form III may further comprise filtering the two solutions of step b) before mixing them. The process for preparing Form III further may further comprise stirring the solution at room temperature after having mixed the two saturated or nearly saturated solutions in step c). The process for preparing Form III may further comprise allowing evaporation of the solution after having the mixing in step c), and preferably after stirring it at room temperature.

The invention provides as well a process for preparing Form IV comprising:

a) preparing a saturated or nearly saturated solution of the compound of formula (I) in 1-methoxy-2-propanol;
b) heating the saturated or nearly saturated solution at the reflux temperature of 1-methoxy-2-propanol;
c) mixing the saturated or nearly saturated solution from step b) with water in a 30%-70% solution/water volume percentage, or in a 4/10 volume ratio.

The process for preparing Form IV may further comprise stirring the solution at room temperature after having mixed it with water in step c). The stirring of the solution at room temperature may be performed during about 4 to about 24 hours, or during about 6 to about 18 hours, or during about 8 to about 16 hours. The process for preparing Form IV may further comprise filtering the solution after having mixed it with water in step c), and preferably after stirring it at room temperature.

The invention provides as well a process for preparing Form V comprising:

a) preparing a saturated or nearly saturated solution of the compound of formula (I) in 2-butanone, and a saturated or nearly saturated solution of the compound of formula (I) in water;
b) heating the two saturated or nearly saturated solutions from step a) to at least 40° C.;
c) mixing the two saturated or nearly saturated solutions from step b) in a 50/50 volume ratio.

The process for preparing Form V may comprise, in step b), heating the two saturated or nearly saturated solutions at about 40° C. to about 70° C., preferably at about 45° C. to about 65° C., more preferably at about 50° C. to about 60° C. The process for preparing Form V may further comprise filtering the two solutions of step b) before mixing them. The process for preparing Form V may further comprise stirring the solution at room temperature after mixing in step c). The process for preparing Form V may further comprise allowing evaporation of the solution after mixing in step c), and preferably after stirring it at room temperature.

The invention provides as well a process for preparing Form VI comprising:

a) preparing a slurry of the compound of formula (I) in water;
b) heating the slurry of step a) at least room temperature for at least about 4 days.

In one embodiment, the process for preparing Form VI comprises, in step a), preparing a solution, preferably a slurry, of the compound of formula (I) in water, wherein the amount ratio of Form I and Form II is about 1/99, 5/95, 10/90, 20/80, 40/60, 50/50, 60/40, 80/20, 90/10, 95/5, or 99/1, preferably about 1/99, 5/95, 10/90, 20/80, 40/60, or 50/50, more preferably about 5/95, 10/90, or 20/80, even more preferably about 10/90.

In another embodiment, the process for preparing Form VI comprises, in step a), preparing a solution of Form I and Form II in water, wherein the amount of water is in excess relative to the amount of Form I and Form II. The process for preparing Form VI may comprise, in step b), heating the solution of step a) at about 30° C. for at least about 4 days, or at about 40° C. for at least about 4 days, or at about 50° C. for at least about 4 days. In one embodiment, the said period of at least 4 days in step b) is a period comprised between about 4 days and about 10 days, in particular between about 4 days and about 6 days.

The invention provides as well a process wherein the obtained crystalline form is isolated by filtration or centrifugation, optionally combined with washing and drying. The starting material used for the processes of the present invention may be any crystalline or amorphous form of the compound of formula (I), including a hydrate thereof. With crystallization processes, the crystalline form of the starting material does not usually affect the final result. With trituration, the final product may vary depending on the starting material. The one of skill in the art would appreciate the convenient manipulation of the starting material to obtain a desirable form with trituration. The present invention is not limited to the starting form used for trituration unless if such form is essential for obtaining another form.

In one embodiment, the solvents employed in the preparation of the crystalline forms of the present invention are pharmaceutically acceptable or pharmaceutically non-acceptable solvents, the former being preferred. Pharmaceutically non-acceptable solvents will have to be removed prior to using the polymorph into a pharmaceutical formulation.

In the mixtures of water and water miscible solvents, the amount of water can vary from about 5% by volume to about 95% by volume, preferably from about 25% to about 75% by volume, more preferably from about 40% to about 60% by volume.

The processes for the production of the crystal forms of the present invention typically include obtaining a crystalline solid material from a solution or dispersion of the compound of formula (I) in a solvent medium, or from slurrying the compound of formula (I), which can be initially in amorphous or crystalline form.

The conditions concerning crystallization may be modified in order to improve the crystallization process or to induce precipitation, and without affecting the form of the polymorph obtained. These conditions include bringing the solution, dispersion, or slurry of the compound of formula (I) and the solvent(s) to a desired concentration, cooling it following a defined cooling/temperature curve, adding crystal seeds, bringing the said solution, dispersion, or slurry to a desired temperature, effecting any suitable pressure, removing and/or separating any undesired material or impurities, drying the formed crystals to obtain the polymorphs in a solid state, if such state is desired.

A preferred way of inducing precipitation is to reduce the solubility of the compound of formula (I). The solubility of the compound may be reduced, for example, by cooling the solution. The solubility of the compound of formula (I) may be reduced by adding an anti-solvent.

Bringing the solution, dispersion, or slurry of the compound of formula (I) and solvents to a desired concentration does not necessarily imply an increase in the concentration of the compound of formula (I). In certain cases, a decrease or no change in concentration of the compound of formula (I) could be preferable. The techniques used for obtaining a desired concentration include, for instance, evaporation by atmospheric distillation, vacuum distillation, fractioned distillation, azeotropic distillation, film evaporation, heating, cooling, other techniques well known in the art and combinations thereof. An optional process for obtaining a desired concentration could as well involve the saturation of the solution of the compound of formula (I) and solvent, for example, by adding a sufficient volume of a non-solvent to the solution to reach the saturation point. Other suitable techniques for saturating the solution include, by way of example, the introduction of additional compound of formula (I) to the solution and/or evaporation of a portion of the solvent from the solution. As referred to herein, a saturated solution encompasses solutions at their saturation points or exceeding their saturation points, i.e. supersaturated. A nearly saturated solution refers to solutions that are near saturation but have not reached their saturation points.

A way to improve the crystallization process of the present invention, in particular of accelerating crystallization, is by seeding with a crystal of the product or scratching the inner surface of the crystallization vessel with a glass rod. Other times, crystallization may occur spontaneously without any inducement. The present invention encompasses both embodiments where crystallization of a particular form of the compound of formula (I) occurs spontaneously, or is induced or accelerated, unless if such inducement or acceleration is critical for obtaining a particular form.

The term "seeding" refers to the addition of a crystalline material to facilitate crystallization. The term "crystal seeds" means powder of a previously obtained crystalline form the compound of formula (I). Particular crystal seeds or seeding material of the present invention, which are useful for preparing Form II, are the following:
  crystal seeds of a mixture of Form II and the amorphous form of the compound of formula (I);
  crystal seeds of Form I; and
  crystal seeds of Form II.

By bringing the said solution, dispersion, or slurry to a desired temperature, one will understand the acts of heating, cooling or leaving at ambient temperature. Warming of the solution, dispersion, or slurry may be necessary to completely dissolve the compound of formula (I).

Removing and/or separating any undesired material or impurities may be performed by purification, filtering, washing, precipitation or similar techniques. Separation, for example, can be conducted by known solid-liquid separation techniques. The filtrations can be performed, amongst other methods, by passing the solution, dispersion, or slurry through paper, sintered glass filter or other membrane material, by centrifugation, or using Buchner style filter, Rosenmund filter or plates, or frame press. Preferably, in-line filtration or safety filtration may be advantageously intercalated in the processes disclosed above, in order to increase the purity of the resulting polymorphic form. Additionally, filtering agents such as silica gel, Celite®, Arbocel®, dicalite diatomite, or the like, may also be employed to separate impurities from the crystals of interest.

Crystals obtained may be also dried, and such drying process may optionally be used in the different crystallization passages, if more than one crystallization passage is applied. Drying procedures include all techniques known to those skilled in the art, such as heating, applying vacuum, circulating air or gas, adding a desiccant, freeze-drying, spray-drying, evaporating, or the like, or any combination thereof.

Processes for crystallization of polymorphs of the compound of formula (I) may embrace multiple combinations of techniques and variations thereof. Crystallization of polymorphs of the compound of formula (I) may be executed by dissolving, dispersing, or slurrying compound of formula (I) at a suitable temperature in the solvent whereby portion of the said solvent evaporates increasing the concentration of the compound of formula (I) in the said solution, dispersion, or slurry, cooling the said mixture, and optionally washing and/or filtering and drying the resulting crystals of the compound of formula (I). Optionally, polymorphs of the compound of formula (I) may be prepared by dissolving, dispersing, or slurrying the compound of formula (I) in a solvent medium, cooling the thus obtained solution, dispersion, or slurry and subsequently filtering and drying the obtained polymorph. Another example of preparation of crystal forms of the compound of formula (I) could be by saturating the compound of formula (I) in the solvent medium, and optionally filtering, washing and drying obtained crystals.

Crystal formation may as well involve more than one crystallization process. In certain cases, one, two or more extra crystallization steps may be advantageously performed for different reasons, such as, to increase the quality of the resulting crystal form. For instance, the polymorphs of the present invention could also be prepared by adding a solvent to an initial starting base material of the compound of formula (I), stirring the solution at a fixed temperature until the substances would be fully dissolved, concentrating the solution by vacuum distillation, and cooling. A first crystallization would take place and the formed crystals would be washed with a solvent, and followed by dissolution of the compound of formula (I) with the solvent to form the desired polymorph. Recrystallization of the reaction mixture would occur, followed by a cooling step from reflux. The formed polymorph would optionally be filtered and allowed to dry.

By dissolving, dispersing, or slurrying the compound of formula (I) in the solvent, one may obtain different degrees of dispersion, such as suspensions, slurries or mixtures; or preferably obtain homogeneous one-phase solutions. The term "suspension" refers to a two-phase system consisting of a finely divided solid, i.e. compound of formula (I) in amorphous, crystalline form, or mixtures thereof, dispersed (suspended) in a liquid or dispersing medium, usually the solvent. The term "slurry" refers to a suspension formed when a quantity of powder is mixed into a liquid in which the solid is only slightly soluble (or not soluble). "Slurrying" refers to the making of a slurry.

Optionally, the solvent medium may contain additives, for example dispersing agents, surfactants or other additives, or mixtures thereof of the type normally used in the preparation of crystalline suspensions. The additives may be advantageously used in modifying the shape of crystal by increasing the leniency and decreasing the surface area.

The solvent medium containing the solid may optionally be stirred for a certain period of time, or vigorously agitated using, for example, a high shear mixer or homogeniser or a combination of these, to generate the desired particle size for the organic compound.

Control of precipitation temperature and seeding may be additionally used to improve the reproducibility of the crystallization process, the particle size distribution and form of the product. As such, the crystallization can be effected without seeding with crystals of the compound of the formula (I) or preferably in the presence of crystals of the compound of the formula (I), which are introduced into the solution by seeding. Seeding can also be effected several times at various temperatures. The amount of the seed material depends on the scale of the experiment and can readily be determined by a person skilled in the art. Typically, the amount of seeding material is about 0.1 to 1 weight % of the amount of crystalline material expected from the reaction.

The time for crystallization in each crystallization step will depend on the conditions applied, the techniques employed and/or solvents used.

Breaking up the large particles or aggregates of particles after crystal conversion may additionally be performed in order to obtain a desired and homogeneous particle size. Accordingly, the crystals, powder aggregates and coarse powder of the polymorphic forms of the compound of formula (I) may be optionally milled and sorted by size after undergoing conversion. Milling or grinding refers to physically breaking up the large particles or aggregates of particles using methods and apparatus well known in the art for particle size reduction of powders. Resulting particle sizes may range from millimeters to nanometers, yielding i.e. nanocrystals, microcrystals. A preferred apparatus for milling or grinding is a fluid energy mill, or micronizer, because of its ability to produce particles of small size in a narrow size distribution.

Pharmaceutical Use of the Crystalline Forms

The present invention further provides a crystalline form of the compound of formula (I), a mixture of two or more crystalline forms of the compound of formula (I), or a mixture of one or more crystalline forms of the compound of formula (I) and the amorphous form of the compound of formula (I), for use as a medicament. In one embodiment, the crystalline form, alone or in any of the above mixtures, for use as a medicament, is selected from Form I, II, III, IV, V, and VI.

The present invention further provides the use of a crystalline form of the compound of formula (I), a mixture of two or more crystalline forms of the compound of formula (I), or a mixture of one or more crystalline forms of the compound of formula (I) and the amorphous form of the compound of formula (I), in the manufacture of a medicament for the treatment of HCV-related conditions. In one embodiment, the crystalline form, alone or in any of the above mixtures, used in the manufacture of a medicament is selected from Form I, II, III, IV, V, and VI.

The present invention provides as well a method of treating a mammal suffering from HCV-related conditions comprising administering a crystalline form of the compound of formula (I), a mixture of two or more crystalline forms of the compound of formula (I), or a mixture of one or more crystalline forms of the compound of formula (I) and the amorphous form of the compound of formula (I), to the mammal in need thereof. In one embodiment, the method of treatment comprises administering a crystalline form, alone or in any of the above mixtures, selected from Form I, II, III, IV, V, and VI.

HCV-related conditions include those pathologic conditions brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and hepatocellular carcinoma (HCC); and for the other pathogenic flaviviruses the diseases include yellow fever, dengue fever, hemorrhagic fever and encephalitis. HCV and the other pathogenic flaviviruses include both wild-type and mutant strains of HCV.

The term "treatment" refers to any treatment of a pathologic condition in a mammal, particularly a human, and includes one or more of the following acts:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the symptoms mediated by the pathologic condition.

The present invention provides furthermore a pharmaceutical composition comprising a crystalline form of the compound of formula (I), a mixture of two or more crystalline forms of the compound of formula (I), or a mixture of one or more crystalline forms of the compound of formula (I) and the amorphous form of the compound of formula (I), and a pharmaceutically acceptable excipient. In one embodiment, the pharmaceutical composition comprises a crystalline form, alone or in any of the above mixtures, selected from Form I, II, III, IV, V, and VI.

Pharmaceutical compositions may be prepared as medicaments to be administered orally, parenterally (including subcutaneously, intramuscularly, and intravenously), rectally, transdermally, bucally, or nasally. Suitable forms for oral administration include powders, granulates, aggregates, tablets, compressed or coated pills, dragees, sachets, hard or gelatin capsules, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art. Although the most suitable administration in any given case will depend on the nature and severity of the condition being treated, the most preferred route of the present invention is oral.

The dosages may be conveniently presented in unit dosage form and prepared by any of the methods well-known in the art. Alternatively, the dosage forms may be presented as one, two, three or four or more subdoses administered at appropriate intervals throughout the day. The unit dosage used is preferably from about 1 mg to about 1000 mg of the compound of formula (I) base equivalent, or from about 5 to about 800 mg, or from about 5 to about 400 mg, or from about 50 to about 600 mg, or from about 100 to about 400 mg.

Pharmaceutical compositions of the present invention comprise the above disclosed polymorphic forms of the compound of formula (I). The pharmaceutical composition may comprise only a single form of the compound of formula (I), or a mixture of various forms of the compound of formula (I), with or without amorphous form. In addition to the active ingredient(s), the pharmaceutical composition comprises one or more excipients or adjuvants.

Examples of suitable excipients are gum arabic, magnesia, magnesium carbonate, potassium phosphate, lactose, glucose, or starch, in particular, corn starch. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the polymorphs of the compound of formula (I), if desired with the substances customary therefor such as solubilizers, emulsifiers or further auxiliaries, are brought into suspension into a liquid carrier such as, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical compositions for administration in the form of aerosols or sprays are, for example, suspensions of the polymorphs of the compound of formula (I) in a pharmaceutically acceptable liquid carrier, such as ethanol or water, or a mixture thereof. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In addition to the ingredients particularly mentioned above, the pharmaceutical compositions of the present invention may include other agents conventional in the art having regard to the type of formulation in question, for example those suitable for oral administration may include flavouring agents or taste masking agents.

As used herein, the term "about" has its conventional meaning. In particular embodiments when in relation to a numerical value, it may be interpreted to mean the numerical value±10%, or ±5%, or ±2%, or ±1%, or ±0.5%, or ±0.1%. In other embodiments, the precise value is meant, i.e. by leaving out the word "about".

EXAMPLES

The following examples are intended to illustrate the present invention and not to limit it thereto.

Example 1

Preparation of 17-[2-(4-isopropylthiazole-2-yl)-7-methoxy-8-methyl-quinolin-4-yloxy]-13-methyl-2,14-dioxo-3,13-diazatricyclo[13.3.0.0$^{4,6}$]octadec-7-ene-4-carboxylic acid (16)

Synthesis of 4-hydroxy-2-(4-isopropylthiazole-2-yl)-7-methoxy-8-methylquinoline (6)

Step 1: synthesis of N-(tert-butyloxycarbonyl)-3-methoxy-2-methylaniline (2)

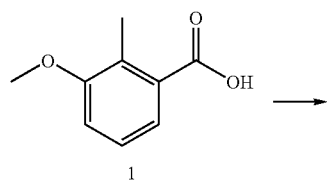

1

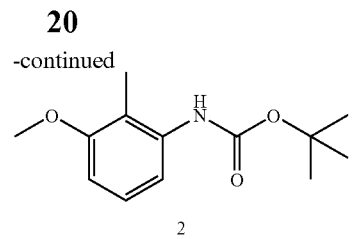

2

Triethylamine (42.4 mL, 302 mmol) was added to a suspension of 3-methoxy-2-methylbenzoic acid (45.6 g, 274 mmol) in dry toluene (800 mL). A clear solution was obtained. Then, dppa (65.4 mL, 302 mmol) in toluene (100 mL) was slowly added. After 1 h at room temperature, the reaction mixture was successively heated at 50° C. for 0.5 h, at 70° C. for 0.5 h then at 100° C. for 1 h. To this solution, t-BuOH (30.5 g, 411 mmol) in toluene (40 mL) was added at 100° C. and the resulting mixture was refluxed for 7 h. The solution was cooled to room temperature then successively washed with water, 0.5 N HCl, 0.5 N NaOH and brine, dried ($Na_2SO_4$), and evaporated to give 67 g of the target product: m/z=237 (M)$^+$.

Step 2: synthesis of 3-methoxy-2-methylaniline (3)

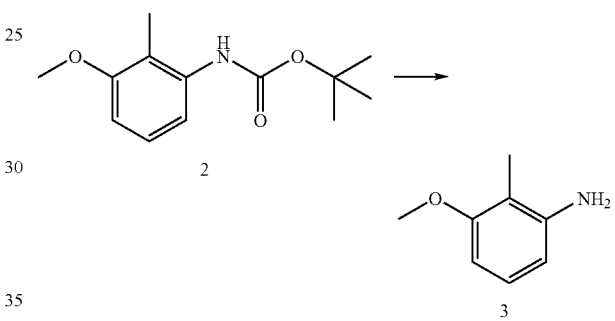

TFA (40.7 mL, 548 mmol) was added to a solution of N-(tert-butyloxycarbonyl)-3-methoxy-2-methylaniline, in dichloromethane (500 mL). After 2 h at room temperature, TFA (40.7 mL, 548 mmol) was added and the resulting mixture was stirred at room temperature overnight. Then, volatiles were evaporated. The residue was triturated with toluene (100 mL) and diisopropylether (250 mL), filtered off and washed with diisopropyl ether (100 mL) to give 56.3 g of the title product as a TFA salt: m/z=138 (M+H)$^+$. The TFA salt was transformed to the free aniline by treatment with NaHCO$_3$.

Step 3: synthesis of (2-amino-4-methoxy-3-methylphenyl)(methyl)ketone (4)

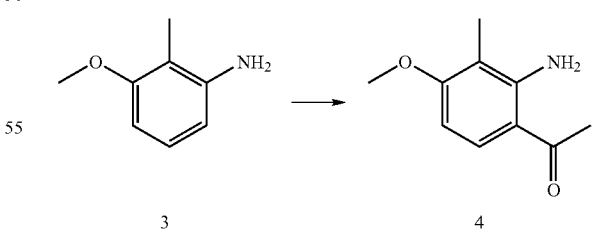

A solution of BCl$_3$ (1.0 M, 200 mL, 200 mmol) in CH$_2$Cl$_2$ was slowly added under nitrogen to a solution of 3-methoxy-2-methylaniline (26.0 g, 190 mmol) in xylene (400 mL). The temperature was monitored during the addition and was kept below 10° C. The reaction mixture was stirred at 5° C. for 0.5 h. Then, dry acetonitrile (13 mL, 246 mmol) was added at 5° C. After 0.5 h at 5° C., the solution was transferred into a dropping funnel and slowly added at 5° C. to a suspension of AlCl₃ (26.7 g, 200 mmol) in CH₂Cl₂ (150 mL). After 45 min at 5° C., the reaction mixture was heated at 70° C. under a nitrogen stream. After evaporation of CH₂Cl₂, the temperature of the reaction mixture reached 65° C. After 12 h at 65° C., the reaction mixture was cooled at 0° C., poured onto ice (300 g), and slowly heated to reflux for 7 h. After 2 days at room temperature, 6 N NaOH (50 mL) was added. The pH of the resulting solution was 2-3. The xylene layer was decanted. The organic layer was extracted with CH₂Cl₂. The xylene and CH₂Cl₂ layers were combined, successively washed with water, 1N NaOH, and brine, dried (Na₂SO₄) and evaporated. The residue was triturated in diisopropyl ether at 0° C., filtered off and washed with diisopropylether to give 13.6 g (40%) of the title product as a yellowish solid: m/z=180 (M+H)⁺.

Step 4: synthesis of 2'-[[(4-isopropylthiazole-2-yl)(oxo)methyl]amino]-4'-methoxy-3'-methylacetophenone (5)

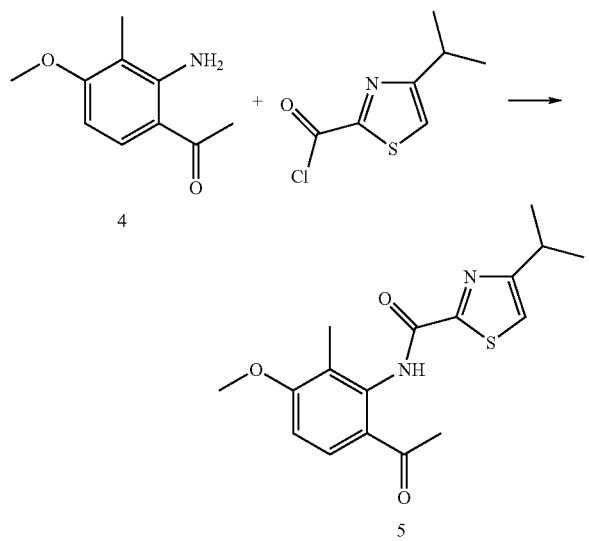

A solution of the compound 4 (18.6 g, 104 mmol) in dioxane (50 mL) was added under nitrogen to a suspension of 4-isopropylthiazole-2-carbonyl chloride in dioxane (250 mL). After 2 h at room temperature, the reaction mixture was concentrated to dryness. Then, the residue was partitioned between an aqueous solution of NaHCO₃ and AcOEt, organic layer was washed with brine, dried (Na₂SO₄), and evaporated. The residue was triturated in diisopropyl ether, filtered off and washed with diisopropyl ether to give 30.8 g (90%) of the title product 5.

Step 5: synthesis of 4-hydroxy-2-(4-isopropylthiazole-2-yl)-7-methoxy-8-methylquinoline (6)

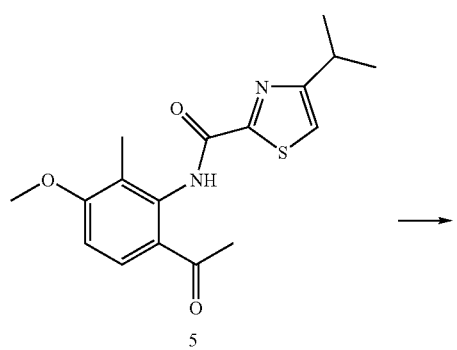

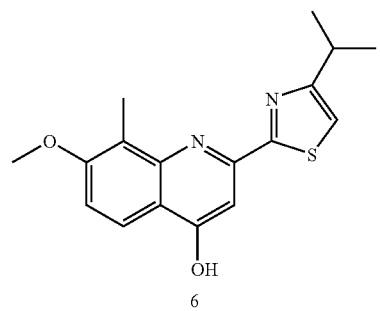

Potassium tert-butoxide (21.8 g, 195 mmol) was added to a suspension of the compound 5 (30.8 g, 92.7 mmol) in tert-butanol. The resulting reaction mixtures was heated at 100° C. overnight. Then, the reaction mixture was cooled at room temperature and diluted with ether (100 mL). The precipitate was filtered off and washed with Et₂O to give a powder (fraction A). The mother liquor was concentrated in vacuo, triturated in ether, filtered off, and washed with ether to give a powder (fraction 2). Fractions 1 and 2 were mixed and poured into water (250 mL). The pH of the resulting solution was adjusted to 6-7 (control with pH paper) with HCl 1N. The precipitate was filtered off, washed with water and dried. Then, the solid was triturated in diisopropyl ether, filtered off and dried to give 26 g (88%) of the compound 6 as a brownish solid: m/z=315 (M+H)⁺.

Synthesis of (hex-5-enyl)(methyl)amine (8)

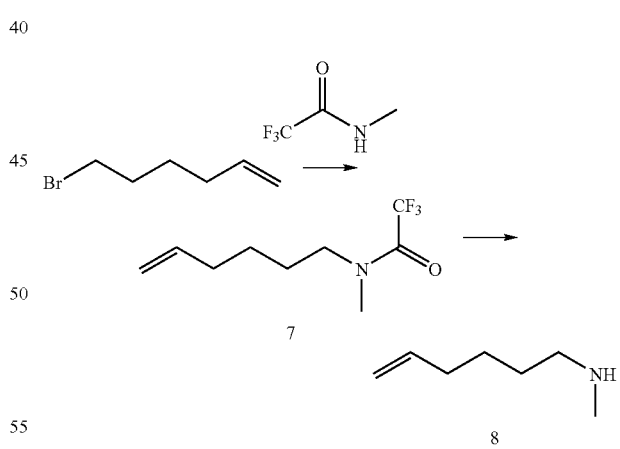

(a) Sodium hydride (1.05 eq) was slowly added at 0° C. to a solution of N-methyl-trifluoro-acetamide (25 g) in DMF (140 mL). The mixture was stirred for 1 h at room temperature under nitrogen. Then, a solution of bromohexene (32.1 g) in DMF (25 mL) was added dropwise and the mixture was heated to 70° C. for 12 hours. The reaction mixture was poured on water (200 mL) and extracted with ether (4×50 mL), dried (MgSO$_4$), filtered and evaporated to give 35 g of the target product 7 as a yellowish oil which was used without further purification in the next step.

(b) A solution of KOH (187.7 g) in water (130 mL) was added dropwise to a solution of 7 (35 g) in methanol (200 mL). The mixture was stirred at room temperature for 12 hours. Then, the reaction mixture was poured on water (100 mL) and extracted with ether (4×50 mL), dried (MgSO$_4$), filtered and the ether was distilled under atmospheric pressure. The resulting oil was purified by distillation under vacuum (13 mm Hg pressure, 50° C.) to give 7.4 g (34%) of the title product 8 as a colourless oil: $^1$H-NMR (CDCl$_3$): δ 5.8 (m, 1H), 5 (ddd, J=17.2 Hz, 3.5 Hz, 1.8 Hz, 1H), 4.95 (m, 1H), 2.5 (t, J=7.0 Hz, 2H), 2.43 (s, 3H), 2.08 (q, J=7.0 Hz, 2H), 1.4 (m, 4H), 1.3 (br s, 1H).

Preparation of 17-[2-(4-isopropylthiazole-2-yl)-7-methoxy-8-methylquinolin-4-yloxy]-13-methyl-2,14-dioxo-3,13-diazatricyclo[13.3.0.0$^{4,6}$]octadec-7-ene-4-carboxylic acid (16)

Step A

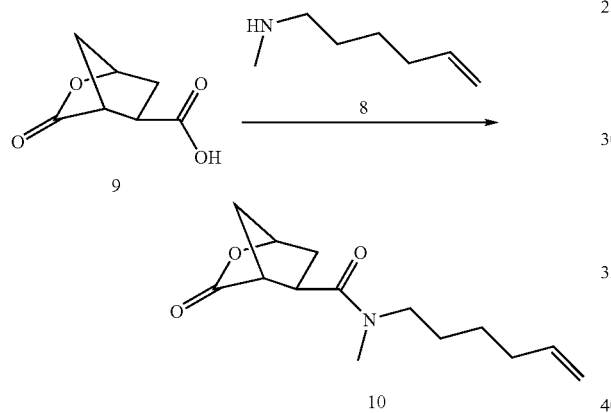

3-Oxo-2-oxa-bicyclo[2.2.1]heptane-5-carboxylic acid 9 (500 mg, 3.2 mmol) in 4 mL DMF was added at 0° C. to HATU (1.34 g, 3.52 mmol) and N-methylhex-5-enylamine (435 mg, 3.84 mmol) in DMF (3 mL), followed by DIPEA. After stirring for 40 min at 0° C., the mixture was stirred at room temperature for 5 h. Then, the solvent was evaporated, the residue dissolved in EtOAc (70 mL) and washed with saturated NaHCO$_3$ (10 mL). The aqueous layer was extracted with EtOAc (2×25 mL). The organic phases were combined, washed with saturated NaCl (20 mL), dried (Na$_2$SO$_4$), and evaporated. Purification by flash chromatography (EtOAc/petroleum ether, 2:1) afforded 550 mg (68%) of the target product 10 as a colorless oil: m/z=252 (M+H)$^+$.

Step B

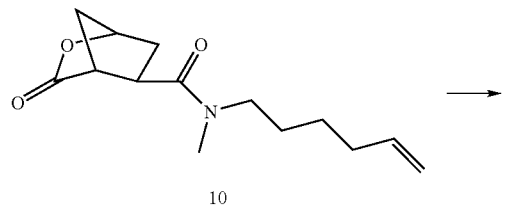

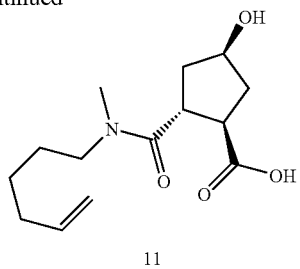

A solution of LiOH (105 mg in 4 ml of water) was added at 0° C. to the lactone amide 10. After 1 h, the conversion was completed (HPLC). The mixture was acidified to pH 2-3 with 1N HCl, extracted with AcOEt, dried (MgSO$_4$), evaporated, co-evaporated with toluene several times, and dried under high vacuum overnight to give 520 mg (88%) of the target product 11: m/z=270 (M+H)$^+$.

Step C

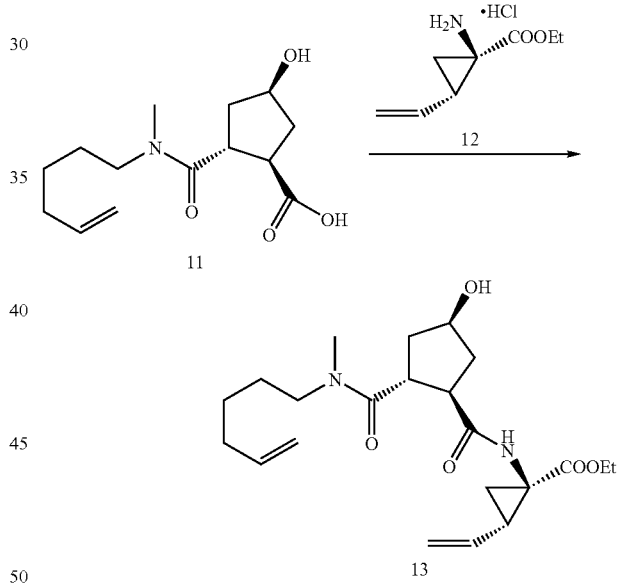

The 1-(amino)-2-(vinyl)cyclopropanecarboxylic acid ethyl ester hydrochloride 12 (4.92 g, 31.7 mmol) and HATU (12.6 g, 33.2 mmol) were added to 11 (8.14 g, 30.2 mmol). The mixture was cooled in an ice bath under argon, and then DMF (100 mL) and DIPEA (12.5 mL, 11.5 mmol) were successively added. After 30 min at 0° C., the solution was stirred at room temperature for an additional 3 h. Then, the reaction mixture was partitioned between EtOAc and water, washed successively with 0.5 N HCl (20 mL) and saturated NaCl (2×20 mL), and dried (Na$_2$SO$_4$). Purification by flash chromatography (AcOEt/CH$_2$Cl$_2$/Petroleum ether, 1:1:1) afforded 7.41 g (60%) of the target product 13 as a colorless oil: m/z=407 (M+H)$^+$.

Step D

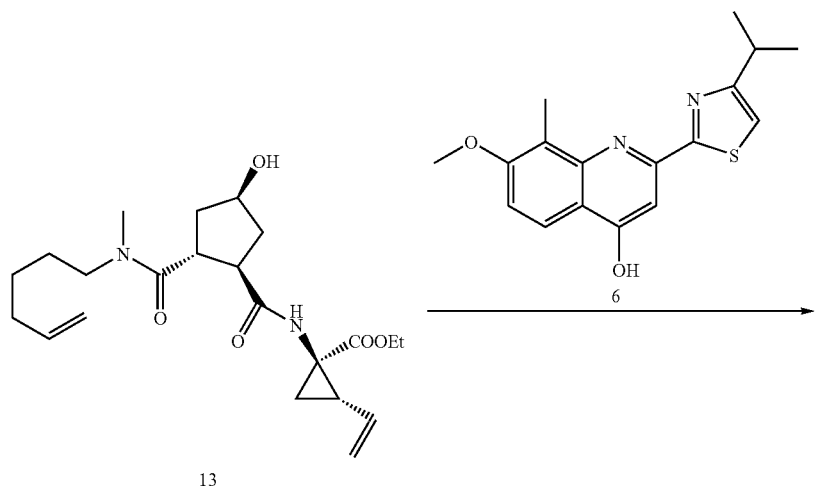

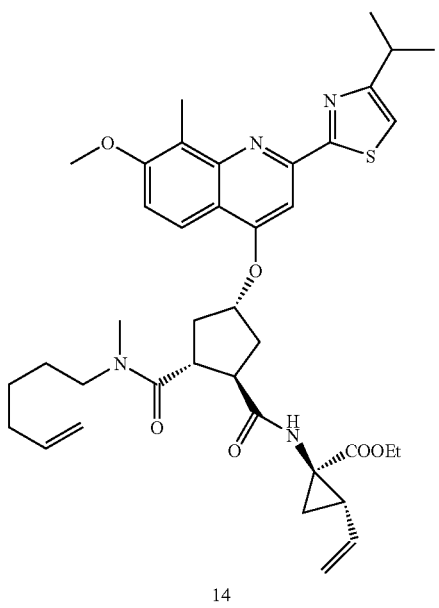

DIAD (1.02 mL, 5.17 mmol) was added at −15° C. under nitrogen atmosphere to a solution of 13 (1.5 g, 3.69 mmol), quinoline 6 (1.39 g, 4.43 mmol) and triphenyl-phosphine (1.26 g, 4.80 mmol) in dry THF (40 mL). After 4.5 h, at −15° C., the reaction mixture was partitioned between ice-cold water and AcOEt, dried ($Na_2SO_4$) and evaporated. The crude material was purified by flash column chromatography (gradient of petroleum AcOEt/$CH_2Cl_2$, 1:9 to 2:8) to give 1.45 g (56%) of the target product 14: m/z=703 (M+H)$^+$.

Step E

Step F

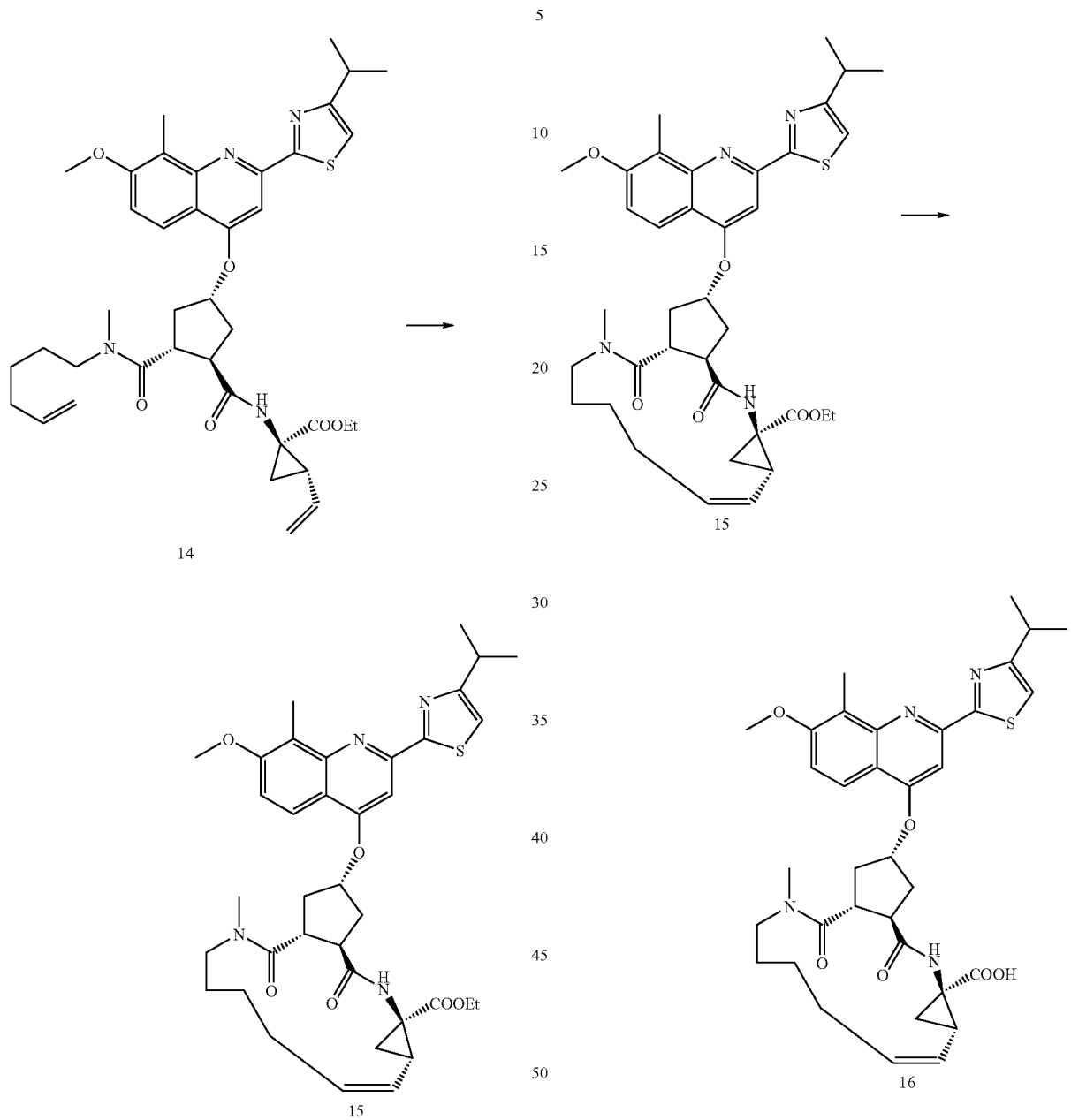

A solution of 14 (1.07 g, 1.524 mmol) and Hoveyda-Grubbs 1$^{st}$ generation catalyst (33 mg, 0.03 eq) in dried and degassed 1,2-dichloroethane (900 mL) was heated at 75° C. under nitrogen for 12 h. Then, the solvent was evaporated and the residue purified by silica gel chromatography (25% EtOAc in CH$_2$Cl$_2$). 620 mg (60%) of pure macrocycle 15 were obtained. m/z=674 (M+H)$^+$. $^1$H NMR (CDCl$_3$): 1.18-1.39 (m, 12H), 1.59 (m, 1H), 1.70-2.08 (m, 5H), 2.28 (m, 1H), 2.38 (m, 1H), 2.62 (m, 2H), 2.68 (s, 3H), 2.83 (m, 1H), 3.06 (s, 3H), 3.19 (sept, J=6.7 Hz, 1H), 3.36 (m, 1H), 3.83 (m, 1H), 3.97 (s, 3H), 4.09 (m, 2H), 4.65 (td, J=4 Hz, 14 Hz, 1H), 5.19 (dd, J=4 Hz, 10 Hz, 1H), 5.31 (m, 1H), 5.65 (td, J=4 Hz, 8 Hz, 1H), 7.00 (s, 1H), 7.18 (s, 1H), 7.46 (d, J=9 Hz, 1H), 7.48 (s, 1H), 8.03 (d, J=9 Hz, 1H).

A solution of lithium hydroxide (1.65 g, 38.53 mmol) in water (15 mL) was added to a stirred solution of ester 15 (620 mg, 0.920 mmol) in THF (30 mL) and MeOH (20 mL). After 16 h at room temperature, the reaction mixture was quenched with NH$_4$Cl sat., concentrated under reduced pressure, acidified to pH 3 with HCl 1N and extracted with CH$_2$Cl$_2$, dried (MgSO$_4$) and evaporated to give 560 mg (88%) of carboxylic acid 16. m/z=647 (M+H)$^+$. $^1$H NMR (CDCl$_3$): 1.11-1.40 (m, 8H), 1.42-1.57 (m, 2H), 1.74 (m, 2H), 1.88-2.00 (m, 2H), 2.13 (m, 1H), 2.28 (m, 1H), 2.40 (m, 1H), 2.59 (m, 2H), 2.67 (s, 3H), 2.81 (m, 1H), 2.97 (s, 3H), 3.19 (m, 1H), 3.31 (m, 1H), 3.71 (m, 1H), 3.96 (s, 3H), 4.56 (dt, J=4 Hz, 12 Hz, 1H), 5.23 (m, 2H), 5.66 (m, 1H), 7.01 (s, 1H), 7.10 (s, 1H), 7.22 (d, J=10 Hz, 1H), 7.45 (s, 1H), 8.00 (d, J=10 Hz, 1H).

Example 2

Preparation of N-[17-[2-(4-isopropylthiazole-2-yl)-7-methoxy-8-methyl-quinolin-4-yloxy]-13-methyl-2,14-dioxo-3,13-diazatricyclo[13.3.0.0^{4,6}]octadec-7-ene-4-carbonyl](cyclopropyl)sulfonamide (17)

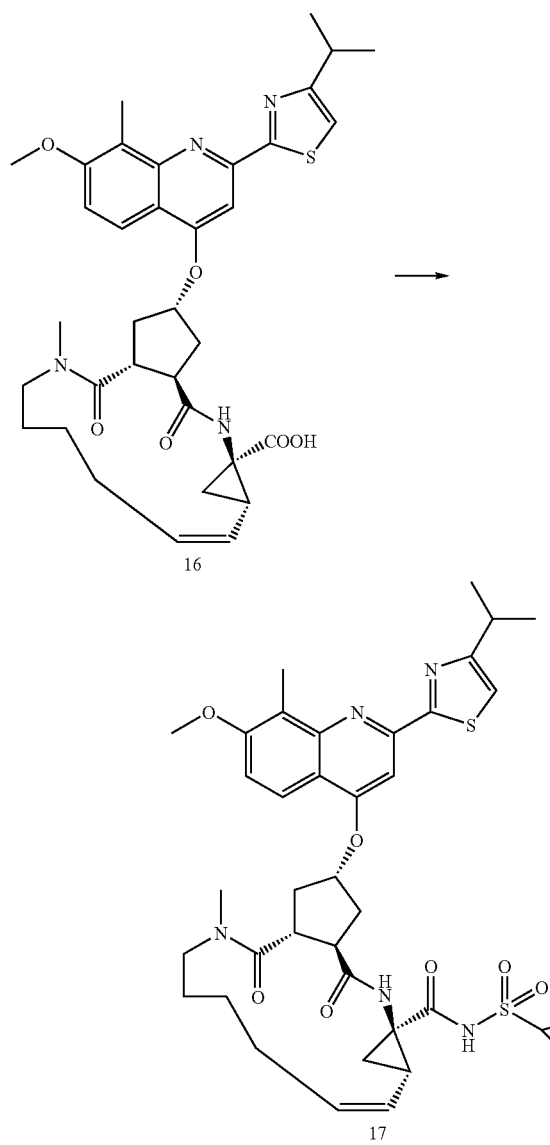

A solution of the compound 16 (560 mg, 0.867 mmol) prepared according to Example 4, and carbonyldiimidazole (308 mg, 1.90 mmol) in dry THF (10 mL) was stirred at reflux under nitrogen for 2 h. The reaction mixture was cooled to room temperature and cyclopropylsulfonamide (400 mg, 3.301 mmol) and DBU (286 mg, 1.881 mmol) were added. This solution was heated at 50° C. for 15 h. Then, the reaction mixture was cooled down at room temperature and concentrated under reduced pressure. The residue was partitioned between $CH_2Cl_2$ and HCl 1 N, the organic layer was washed with brine, dried ($MgSO_4$) and evaporated. Purification by flash chromatography (gradient of EtOAc (0 to 25%) in $CH_2Cl_2$) afforded 314 mg of an off-white solid which was further washed with water, then isopropylether, and dried in the vacuum oven to deliver 282 mg (40%) of the pure title product 17, which is the compound of formula (I), as a white powder: m/z=750 (M+H)$^+$. $^1$H NMR ($CDCl_3$): 0.99-1.52 (m, 14H), 1.64-2.05 (m, 4H), 2.77 (m, 1H), 2.41 (m, 2H), 2.59 (m, 2H), 2.69 (s, 3H), 2.92 (m, 2H), 3.04 (s, 3H), 3.19 (m, 1H), 3.40 (m, 2H), 3.98 (s, 3H), 4.60 (t, J=13 Hz, 1H), 5.04 (t, J=11 Hz, 1H), 5.37 (m, 1H), 5.66 (m, 1H), 6.21 (s, 1H), 7.02 (s, 1H), 7.22 (d, J=10 Hz, 1H), 7.45 (s, 1H), 7.99 (d, J=10 Hz, 1H), 10.82 (broad s, 1H).

Example 3

Preparation of Polymorph I 2 g of a mixture of polymorph I and II was refluxed in a small amount of 1-butanol. To the boiling slurry, small portions of 1-butanol were added until a clear solution was obtained. At this point, the amount of 1-butanol added was 17.85 L/mol. The solution was stirred further and cooled spontaneously to room temperature over the weekend. The solid material was recovered by filtration and washed with 2 times 5 mL 1-butanol. The XPRD analysis showed that the obtained material was crystalline polymorph I.

Example 4

Preparation of the Compound of Formula (I) in Amorphous Form 1 g of a mixture of polymorph I and II was dissolved in dichloromethane (120 mL). The resulting clear solution was filtered over a P4 filter (with a pore size between 10-16 μm) and evaporated to dryness (rotavapor; 40° C.; 750 to 50 mbar) and this yielded amorphous compound (I), confirmed by XPRD analysis (see FIG. 21).

Example 5

Preparation of Polymorph II 3.1 By Seeding with Polymorph II

To 1 g amorphous material of the compound (I) (as obtained from Example 2), 25 mL of 2-PrOH was added and the suspension was stirred at room temperature for about 15 minutes. After this, a small amount of seeding material of polymorph II was added and the slurry was stirred further at room temperature. Within 15 minutes, a white material started to form in the suspension that was stirred further over the weekend. The white precipitate was filtered off, washed with 10 mL 2-prOH and dried over night at 60° C./vacuum.

The mass recovery was 92 wt % and the XPRD analysis showed that the obtained material was crystalline polymorph II with potentially small traces of polymorph I according to IR-analysis.

3.2 By Seeding with Polymorph I 0.2 g of a mixture of polymorph I and II was dissolved in dichloromethane (10 mL). The resulting clear solution was evaporated to dryness (rotavapor) and the residue was scratched from the wall of the flask. To this amorphous material, 5 mL of 2-PrOH (25 mL/g) was added and the suspension was stirred at room temperature for about 15 minutes. After this, seeding material of polymorph I (as obtained from any of the Examples 3, 10, or 11) was added and the slurry was stirred further at room temperature. A white precipitate started to form in the suspension, which was stirred further over night. The precipitate was filtered off, washed with a small amount of 2-PrOH and dried over night at 60° C./vacuum.

A white solid was recovered and XPRD analysis showed that the obtained material was crystalline polymorph II with clear traces of polymorph I.

3.3 By Using a Multi-Gram Scale (20 g Scale) Procedure $1^{st}$ Crop:

About 20 g of a mixture of polymorph I and II was dissolved in dichloromethane (100 mL) and filtered over a P4 filter (with a pore size between 10-16 µm). The resulting clear solution was evaporated to dryness (rotavapor; 40° C.; 750 to 50 mbar). To the residue, 250 mL of 2-PrOH (12.5 ml/g) was added and the suspension was stirred at room temperature for about 15 minutes. After this, seeding material of polymorph II (as obtained from Example 12) was added and the suspension was stirred further at room temperature. A white precipitate started to form in the suspension, which was stirred further over night. The precipitate was filtered off, washed with 10 mL 2-PrOH and dried over night at 60° C./vacuum.

7.8 g of a white solid was recovered and XPRD analysis showed that the obtained material was crystalline polymorph II.

$2^{nd}$ Crop:

The mother liquor, together with the material that remained on the wall of the reactor was collected and the solvent was evaporated. Half-way the evaporation, a sample of the suspension was taken, filtered, dried and analyzed and appeared to be mainly amorphous material with polymorph I and II present together with some unidentified crystalline material(s). The rest of the suspension was evaporated to dryness (mass=11 g).

This was dissolved in dichloromethane and filtered over a P4 filter. The resulting clear solution was evaporated to dryness (rotavap; 40° C.; 750 to 50 mbar). To this amorphous material, 275 ml of 2-PrOH (25 mL/g) was added and the suspension was stirred at room temperature for about 15 minutes. After this, seeding material of polymorph II (as obtained from Example 10) was added and the slurry was stirred further at room temperature. Within 15 minutes, a white precipitate started to form in the suspension which was stirred further over night. The precipitate was filtered off, washed with two times 10 mL 2-PrOH and dried over night at 60° C./vacuum. The mother liquor, together with the materials that remained on the wall of the reactor were collected and the solvent was evaporated to dryness (mass=6.51 g).

4.6 g of a white solid was recovered and XPRD analysis showed that the obtained material was crystalline polymorph II.

Example 6

Preparation of Polymorph III

Two saturated solutions of polymorph II in acetonitrile and in water at 50° C. were prepared. These solutions were filtered after 1.5 hours at 50° C. 225 µL of each filtrate were dispensed in the same well and the mixture was allowed to crystallize at room temperature, and the solvent was evaporated at room temperature until dryness. Form III was obtained.

Example 7

Preparation of Polymorph IV 40 mg of polymorph 1 and 4 mL 1-methoxy-2-propanol were heated to reflux while stirring. 10 ml water was added to the solution and the solution was allowed to crystallize at room temperature overnight while stirring. The precipitate was filtered using a Millipore filter and the product was dried at room temperature for 1 hour. Form IV was obtained.

Example 8

Preparation of Polymorph V

Two saturated solutions of polymorph II in 2-butanone and in water were prepared at 50° C. These solutions were filtered after 1.5 hours at 50° C. 225 µL of each filtrate were dispended in a same well and the mixture was allowed to crystallize at room temperature, and the solvent was evaporated at room temperature until dryness. Form V was obtained.

Example 9

Preparation of Polymorph VI

A slurry was prepared by weighing 15 mg of polymorph II and 1.5 mg polymorph I into an HPLC vial. 100 µL water was added and the closed vial was stored for 4 days at 30° C. and 7 days at 40° C. The product was dried on a paper filter at room temperature. Form VI was obtained.

Example 10

Transformation of a Mixture of Polymorphs II and I into Polymorph I Using a Slurry Procedure 1 g of a mixture of polymorph I and II was refluxed in parallel experiments in a fixed amount of solvent (11 L/mol of each MeOH, EtOH, EtOH/H$_2$O, 2-PrOH, and 1-butanol). The slurries were refluxed for approximately 2 h and were allowed to cool spontaneously to room temperature and stirred over the weekend. For a separate parallel reaction in 2-propanol, a hot filtration was performed. The solid material was recovered by filtration and washed with 2 times 5 mL of the corresponding solvent.

In Table 4, there is shown for each experiment, the solvent used, the recovery yield, the purity of the obtained polymorphs or mixture thereof, and the type of polymorphism.

TABLE 4

| Experiment no. | Solvent | Recovery (wt %) | Polymorph |
|---|---|---|---|
| 8a | MeOH | 89 | I |
| 8b | EtOH | 94 | I |
| 8c | EtOH/H$_2$O (volume ratio 95/5) | 91 | I |
| 8d | 2-PrOH | 91 | I + II[(1)] |
| 8e | 2-PrOH[(2)] | 80 | I + II[(1)] |
| 8f | 1-BuOH | 90 | I |

[(1)] A clear enrichment in polymorph II was observed
[(2)] Isolation of material through hot filtration

Example 11

Transformation of Polymorph II into Polymorph I Using a Slurry Procedure Monitored by Process Analytical Technology (PAT)

A 250 mL MultiMax-reactor was loaded with 3.7 g of polymorph II and 100 mL 2-propanol was added (20.3 L/mol). The reactor was installed into the MultiMax and the Raman-, NIR- and FTIR-probes were inserted into the suspension which was stirred at room temperature. The reactor was shielded from daylight and the measurements were started. After approximately 30 minutes, the reaction was heated to 80° C. at a rate of about 2°/min. After about 1 hour at 80° C., a clear solution was observed and therefore, an extra amount of 1.85 g polymorph II was added to the reactor bringing the total amount of polymorph II to 5.55 g. At this point, 18 mL of solvent/g of polymorph II was used (compared to 15 mL/g in the earlier slurry experiments).

The slurry was stirred at 80° C. over night. After approximately 20 hours, 1.11 g of polymorph II, 20% of the original amount, was added to the hot suspension, which was stirred for about another 2 h. After this the reaction mixture was cooled to room temperature and filtered.

Raman spectra were collected every 2 minutes with a RXN1/785 Raman spectrometer of Kaiser Optical Systems in combination with an immersion probe. Principle component analysis (PCA) (no data-pretreatment, range 1200-1400 cm$^{-1}$) was used to analyze the variation in time. The first 2 principle components showed similarity with the spectra of polymorph I and II. See Table 5 below.

TABLE 5

| Polymorph I | PCA of the first principle component (in cm$^{-1}$) | Polymorph II | PCA of the second principle component (in cm$^{-1}$) |
|---|---|---|---|
| 1370 | 1370 | 1378 | 1378 |
| 1330 | 1330 | 1335 | 1335 |
| 1260 | 1260 | 1265 | 1265 |

A time plot of the absorbance units showed the transformation of polymorph II to polymorph I. During the first 4 hours, dissolution of polymorph II was taking place. 1 hour later, polymorph I was being formed and the transformation was finished after another 5 hours. Adding an additional amount of polymorph II (at 20 hours) resulted in a fast transformation of polymorph II to I.

Near-infrared (NIR) spectra were collected every 2 minutes with a Bruker-Matrix-F NIR spectrometer (32 scans, resolution 4 cm$^{-1}$, 10000 to 5000 cm$^{-1}$) and a reflection probe (Solvias Reflector). Spectra of a slurry of polymorph I and II were calibrated by the value 1 and 2 respectively (PLS, 6800-5600 cm$^{-1}$, vector normalization and rank=1). This model was used to monitor trend changes in polymorphism over time. During the first 4 hours, dissolution of polymorph II was taking place. 1 hour later, polymorph I was being formed and the transformation was finished after another 5 hours.

XPRD analysis of the isolated product showed that the obtained material was crystalline polymorph I. It was observed with RAMAN and NearIR that the conversion of Pol II into Pol I started after about 5 hours and took about 3 hours. Addition of extra Pol II after full conversion to Pol I resulted in an immediate start of the conversion of Pol II into Pol I.

This experiment was repeated in a 2-propanol/dichloromethane (97/3) (v/v) mixture but this gave identical results concerning induction period, conversion time and final product polymorphism.

Example 12

Preparation of Polymorph II Through Crystallization with or without Seeding a) 20 mL of solution of the compound of formula (I) in dichloromethane (10 L/mol) was introduced into a 100 mL flask. The solution was stirred at room temperature and 20 ml of isopropanol was added. This solution was partially evaporated (using a rotavap) under a moderate vacuum (750 mbar) at room temperature until most of the dichloromethane was removed resulting in a clear solution.

b) To 2 mL of the solution obtained under a), a small amount of seeding material of Polymorph I (as obtained from any of the examples 3, 10, or 11) was added at room temperature. Immediately, a voluminous white precipitate was formed that was filtered off, washed with 2 mL 2-propanol and dried at 60° C. under atmospheric pressure (Fraction 9.1).

c) 2 mL of the solution obtained under a), was cooled to 0° C. and stirred during 14 hours at this temperature. An amount of sticky material was formed which was isolated by decantation, washed and dried for 72 h at 60° C. under atmospheric pressure. A solid material was obtained (Fraction 9.2).

d) The solution of the compound of formula (I) obtained under a) was kept 3 days at room temperature. The formed precipitate was filtered off and the isolated solid material consisted of hemispherical particles together with fine white needle like material. Both fractions were collected separately:
Fraction 9.3: needle like material
Fraction 9.4: hemispherical-shaped solid
Both samples were dried for 14 h at 60° C. under atmospheric pressure.

XPRD analysis (see FIGS. 27-30) showed that the obtained materials were crystalline.

Example 13

Determination of the Solubility of Form I and Form II in Different Solvents

An excess of product (Form I or Form II, where appropriate) was shaken with the relevant solvent during 24 hours at 20° C. After filtration, the concentration of the product in solution was determined with UV spectrometry. The solubility results for Form I and Form II are shown in the table below.

TABLE 6

| solvent | Solubility of Form I in g/100 mL of solution | Solubility of Form II in g/100 mL of solution |
|---|---|---|
| water (pH = 5.0) | <0.001 | n.d. |
| methanol | 0.056 | 0.29 |
| ethanol | 0.050 | 0.17 |
| 2-propanol | 0.027 | 0.11 |
| 2-propanone | 0.66 | 1.2 |
| toluene | 0.086 | 0.43 |
| 4-methyl-2-pentanone | 0.28 | 0.81 |
| 2-butanone | 0.87 | 2.5 |
| 1-methoxy-2-propanol | 0.82 | 1.6 |
| acetonitrile | 0.075 | 0.20 |
| 1-butanol | n.d. | 0.31 |
| dichloromethane | 8.5 | n.d. |
| ethyl acetate | 0.21 | n.d. |
| N,N-dimethylacetamide* | >20 | n.d. |
| N,N-dimethylacetamide | 16 | n.d. |
| tetrahydrofuran | 7.0 | n.d. |
| acetic acid | 1.7 | n.d. |
| acetic acid/water (10/90) (v/v) (pH = 2.2) | <0.001 | n.d. |
| methanol/dichloromethane (50/50) (v/v) | 8.3 | n.d. |
| 2-propanol/dichloromethane (97/3) (v/v) | 0.045 | 0.19 |
| ethanol/water (95/5) (v/v) | 0.078 | 0.27 |

*125 mg of Form I was dissolved in 0.5 mL of N,N-dimethylacetamide
n.d. = not determined

The invention claimed is:

1. A compound of formula (I):

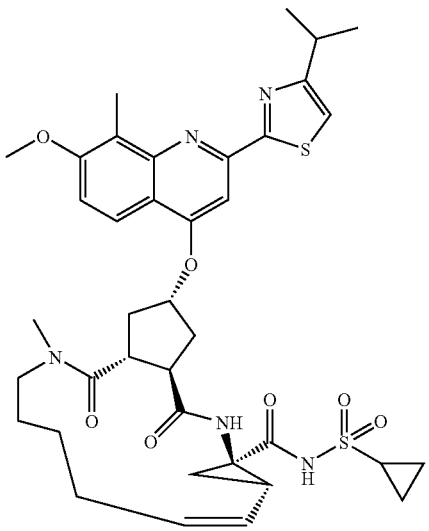

in solid state characterized in that it is in crystalline form.

2. The compound of claim 1 wherein the crystalline form has an X-ray powder diffraction pattern comprising peaks at 8.5°±0.2°, 10.7°±0.2°, 13.7°±0.2°, 14.8°±0.2° and 17.1°±0.2° two theta (Form I).

3. The compound of claim 2 wherein the crystalline form has an IR pattern comprising peaks at 3405±1 $cm^{-1}$, 3066±1 $cm^{-1}$, 1517±1 $cm^{-1}$, 1427±1 $cm^{-1}$, 1301±1 $cm^{-1}$, 1285±1 $cm^{-1}$, 1149±1 $cm^{-1}$, 1132±1 $cm^{-1}$, 1111±1 $cm^{-1}$, 975±1 $cm^{-1}$, 956±1 $cm^{-1}$, and 800±1 $cm^{-1}$ (Form I).

4. The compound of claim 1 wherein the crystalline form has an X-ray powder diffraction pattern comprising peaks at 4.6°±0.2°, 6.5°±0.2°, 10.2°±0.2°, 12.9°±0.2° and 14.4°±0.2 two theta (Form II).

5. The compound of claim 4 wherein the crystalline form has an IR pattern comprising peaks at 1592 $cm^{-1}$±1 $cm^{-1}$ (Form II).

6. The compound of claim 1 wherein the crystalline form has an X-ray powder diffraction pattern comprising peaks at 6.5°±0.2°, 9.8°±0.2° and 17.8°±0.2° two theta (Form III).

7. The compound of claim 6 wherein the crystalline form has an IR pattern comprising peaks at 3120±1 $cm^{-1}$, 2870±1 $cm^{-1}$, and 1063 $cm^{-1}$±1 $cm^{-1}$ (Form III).

8. The compound of claim 1 wherein the crystalline form has an X-ray powder diffraction pattern comprising peaks at 5.6°±0.2°, 9.6°±0.2°, 11.8°±0.2°, 15.9°±0.2° and 17.1°±0.2° two theta (Form IV).

9. The compound of claim 8 wherein the crystalline form has an IR pattern comprising peaks at 1369±1 $cm^{-1}$ and 846±1 $cm^{-1}$ (Form IV).

10. The compound of claim 1 wherein the crystalline form has an X-ray powder diffraction pattern comprising peaks at 9.6°±0.2° and 19.0°±0.2° two theta (Form V).

11. The compound of claim 1 wherein the crystalline form has an X-ray powder diffraction pattern comprising peaks at 4.4°±0.2°, 6.5°±0.2°, 9.9°±0.2°, 10.5°±0.2° and 12.9°±0.2° two theta (Form VI).

12. A mixture of two or more crystalline forms of the compound of formula (I),

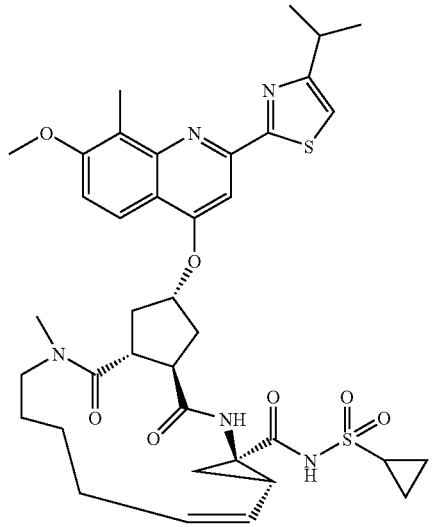

wherein the crystalline forms are selected from Form I according to claim 3,

Form II having an X-ray powder diffraction pattern comprising peaks at 4.6°±0.2°, 6.5°±0.2°, 10.2°±0.2°, 12.9°±0.2° and 14.4°±0.2 two theta and an IR pattern comprising peaks at 1592 $cm^{-1}$±1 $cm^{-1}$; Form III having an X-ray powder diffraction pattern comprising peaks at 6.5°±0.2°, 9.8°±0.2° and 17.8°±0.2° two theta and an IR pattern comprising peaks at 3120±1 $cm^{-1}$, 2870±1 $cm^{-1}$, and 1063 $cm^{-1}$±1 $cm^{-1}$; Form IV having an X-ray powder diffraction pattern comprising peaks at 5.6°±0.2°, 9.6°±0.2°, 11.8°±0.2°, 15.9°±0.2° and 17.1°±0.2° two theta and an IR pattern comprising peaks at 1369±1 $cm^{-1}$ and 846±1 $cm^{-1}$; Form V having an X-ray powder diffraction pattern comprising peaks at 9.6°±0.2° and 19.0°±0.2° two theta; and Form VI having an X-ray powder diffraction pattern comprising peaks at 4.4°±0.2°, 6.5°±0.2°, 9.9°±0.2°, 10.5°±0.2° and 12.9°±0.2° two theta.

13. The mixture according to claim 12, wherein the mixture comprises Form II and Form I of the compound of formula (I).

14. The mixture according to claim 12, wherein the mixture comprises Form III and Form II of the compound of formula (I).

15. A mixture of one or more crystalline forms of the compound of formula (I) and the amorphous form of the compound of formula (I), wherein the crystalline forms are selected from Form I according to claim 3, Form II having an X-ray powder diffraction pattern comprising peaks at 4.6°±0.2°, 6.5°±0.2°, 10.2°±0.2°, 12.9°±0.2° and 14.4°±0.2 two theta and an IR pattern comprising peaks at 1592 $cm^{-1}$±1 $cm^{-1}$; Form III having an X-ray powder diffraction pattern comprising peaks at 6.5°±0.2°, 9.8°±0.2° and 17.8°±0.2° two theta and an IR pattern comprising peaks at 3120±1 $cm^{-1}$, 2870±1 $cm^{-1}$, and 1063 $cm^{-1}$±1 $cm^{-1}$; Form IV having an X-ray powder diffraction pattern comprising peaks at 5.6°±0.2°, 9.6°±0.2°, 11.8°±0.2°, 15.9°±0.2° and 17.1°±0.2° two theta and an IR pattern comprising peaks at 1369±1 $cm^{-1}$ and 846±1 $cm^{-1}$; Form V having an X-ray powder diffraction pattern comprising peaks at 9.6°±0.2° and 19.0°±0.2° two theta; and Form VI having an X-ray powder diffraction pattern comprising peaks at 4.4°±0.2°, 6.5°±0.2°, 9.9°±0.2°, 10.5°±0.2° and 12.9°±0.2° two theta.

16. The mixture according to claim 15, wherein the mixture comprises Form II and the amorphous form of the compound of formula (I).

17. A process for preparing the crystalline form according to any one of claims 2-3 (Form I) comprising:
a) dissolving compound of formula (I) in 1-butanol or 2-propanol while heating at the reflux temperature of the solvent; and
b) allowing spontaneous cooling.

18. A process for preparing the crystalline form according to any one of claims 2-3 (Form I) comprising:
slurrying Form II in an alcoholic solvent selected from 2-propanol, ethanol, 1-butanol, methanol, a mixture of alcohol (such as methanol, ethanol, propanol, isopropanol, 1-butanol, or 2-butanol) and dichloromethane or water, or a mixture thereof, at the reflux temperature of the alcoholic solvent; or
slurrying a mixture of Form I and Form II in a solvent selected from 2-propanol, methyl isopropylketone (MIK), THF, acetonitrile, ethanol, acetone, 1-methoxypropan-2-ol (1-M-2-P), methyl ethylketone (MEK), dichloromethane, 1-butanol, methanol, a mixture of alcohol (such as methanol, ethanol, propanol, isopropanol, 1-butanol, or 2-butanol) and dichloromethane or water, or a mixture thereof, at a temperature of at least about 30° C.

19. A process for preparing the crystalline form according to any one of claims 4-5 (Form II) comprising:
a) preparing a suspension of the amorphous form of the compound of formula (I) in isopropanol;
b) stirring the suspension at room temperature; and
c) seeding the suspension with crystal seeds of Form II or Form I.

20. A process for preparing the crystalline form according to any one of claims 4-5 (Form II) comprising:
a) dissolving compound of formula (I) in 2-propanol; and
b) keeping the solution from step a) at room temperature during at least 1 day, or at around 0° C. during at least 4 hours.

21. A process for preparing the crystalline form according to any one of claims 6-7 (Form III) comprising:
a) preparing a saturated or nearly saturated solution of the compound of formula (I) in acetonitrile, and a saturated or nearly saturated solution of the compound of formula (I) in water;
b) heating the two saturated or nearly saturated solutions from step a) at least 40° C.;
c) mixing the two saturated or nearly saturated solutions from step b) in a 50/50 volume ratio.

22. A process for preparing the crystalline form according to any one of claims 8-9 (Form IV) comprising:
a) preparing a saturated or nearly saturated solution of the compound of formula (I) in 1-methoxy-2-propanol;
b) heating the saturated or nearly saturated solution at the reflux temperature of 1-methoxy-2-propanol;
c) mixing the saturated or nearly saturated solution from step b) with water in a 4/10 volume ratio.

23. A process for preparing the crystalline form according to claim 10 (Form V) comprising:
a) preparing a saturated or nearly saturated solution of the compound of formula (I) in 2-butanone, and a saturated or nearly saturated solution of the compound of formula (I) in water;
b) heating the two saturated or nearly saturated solutions from step a) at least 40° C.;
c) mixing the two saturated or nearly saturated solutions from step b) in a 50/50 volume ratio.

24. A process for preparing the crystalline form according to claim 11 (Form VI) comprising:
a) preparing a slurry of the compound of formula (I) in water;
b) heating the slurry of step a) at least room temperature for at least 4 days.

25. A pharmaceutical composition comprising a crystalline form of the compound of formula (I),

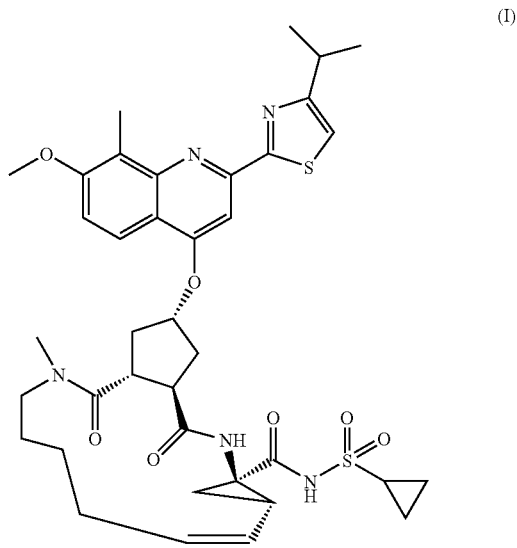

(I)

a mixture of two or more crystalline forms of the compound of formula (I), and a pharmaceutically acceptable excipient.

26. The pharmaceutical composition according to claim 25 wherein the crystalline forms are selected from Form I according to claim 3,
Form II having an X-ray powder diffraction pattern comprising peaks at 4.6°±0.2°, 6.5°±0.2°, 10.2°±0.2°, 12.9°±0.2° and 14.4°±0.2 two theta and an IR pattern comprising peaks at 1592 cm$^{-1}$±1 cm$^{-1}$; Form III having an X-ray powder diffraction pattern comprising peaks at 6.5°±0.2° 9.8°±0.2° and 17.8°±0.2° two theta and an IR pattern comprising peaks at 3120±1 cm$^{-1}$, 2870±1 cm$^{-1}$, and 1063 cm$^{-1}$±1 cm$^{-1}$; Form IV having an X-ray powder diffraction pattern comprising peaks at 5.6°±0.2° 9.6°±0.2° 11.8°±0.2° 15.9°±0.2° and 17.1°±0.2° two theta and an IR pattern comprising peaks at 1369±1 cm$^{-1}$ and 846±1 cm$^{-1}$; Form V having an X-ray powder diffraction pattern comprising peaks at 9.6°±0.2° and 19.0°±0.2° two theta; and Form VI having an X-ray powder diffraction pattern comprising peaks at 4.4°±0.2°, 6.5°±0.2°, 9.9°±0.2°, 10.5°±0.2° and 12.9°±0.2° two theta.

* * * * *